US009175049B2

(12) United States Patent
Stabel et al.

(10) Patent No.: US 9,175,049 B2
(45) Date of Patent: Nov. 3, 2015

(54) RECOMBINANT MYCOBACTERIUM AVIUM SUBSP. PARATUBERCULOSIS PROTEINS INDUCE IMMUNITY AND PROTECT AGAINST INFECTION

(71) Applicant: The United States of America, as represented by the Secretary of Agriculture, Washington, DC (US)

(72) Inventors: Judith R. Stabel, Ames, IA (US); John P. Bannantine, Ames, IA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/038,077

(22) Filed: Sep. 26, 2013

(65) Prior Publication Data

US 2014/0112949 A1   Apr. 24, 2014

Related U.S. Application Data

(60) Provisional application No. 61/717,723, filed on Oct. 24, 2012.

(51) Int. Cl.
| | | |
|---|---|---|
| *C07K 14/35* | (2006.01) | |
| *A61K 39/04* | (2006.01) | |
| *A61K 39/00* | (2006.01) | |

(52) U.S. Cl.
CPC ............ *C07K 14/35* (2013.01); *A61K 39/04* (2013.01); *A61K 2039/552* (2013.01); *A61K 2039/6068* (2013.01)

(58) Field of Classification Search
CPC ........ A61K 39/00; A61K 39/02; A61K 39/04
USPC ........... 424/184.1, 185.1, 192.1, 234.1, 248.1
See application file for complete search history.

(56) References Cited

U.S. PATENT DOCUMENTS

| 7,867,704 B2 | 1/2011 | Kapur et al. |
| 2009/0099083 A1 | 4/2009 | Chang |
| 2011/0274712 A1 | 11/2011 | Aldwell et al. |

FOREIGN PATENT DOCUMENTS

| WO | 2007/075308 A2 | 7/2007 |
| WO | 2010/051210 A1 | 5/2010 |
| WO | 2010/124154 A1 | 10/2010 |

OTHER PUBLICATIONS

Barnhill, Alison E., et al., "Immunologic responses to Mycobacterium avium subsp. paratuberculosis protein cocktail vaccines in a mouse model", Conference for Research Workers in Animal Disease, presented Dec. 2010.

Sriasih, Made, "A study on secreted proteins of Mycobacterium avium subspecies paratuberculosis vaccine strain 316F", 2010, Massey University, Palmertson North, New Zealand.

Li, Lingling, et al. "Rapid Expression of Mycobacterium avium subsp. paratuberculosis Recominbant Proteins for Antigen Discovery", Clinical and Vaccine Immunology, vol. 14, No. 1, Jan. 2001, pp. 102-105.

Bannantine, John P., et al,, "Early antibody response against Mycobacterium avium subspecies paratuberculosis antigens in subclinical cattle", Proteome Science, BioMed Central, http://www.proteomesci.com/content/6/1/5, Jun. 5, 2008.

Bannantine, J.P. and J. R. Stabel, "Killing of Mycobacterium avium subspecies paratuberculosis within macrophages" BMC Microbiology (2002) 2(2):1-7.

Bannantine, J.P. et al. "MAP1272c Encodes an NIpC/P60 Protein, an Antigen Detected in Cattle with Johne's Disease" Clinical and Vaccine Immunology (2012) 19(7):1083-1092.

Bannantine, J.P. and J. R. Stabel, "Killing of Mycobacterium avium subspecies paratuberculosis within macrophages"BMC Microbiology (2002) 2(2):1-7.

Bannantine, J.P. et al. "MAP1272c Endcodes an NIpC/P60 Protein, an Antigen Detected in Cattle with Johne's Disease" Clinical and Vaccine Immunology (2012) 19(7):1083-1092.

Bannantine, J.P. and J. R.Stabel, "Killing of Mycobacterium avium subspecies paratuberculosis within macrophages" BMC Microbiology (2002) 2(2):1-7.

Bannantine, J.P. et al "MAP1272c Encodes an NIpC/P60 Protein, an Antigen Detected in Cattle with Johne's Disease" Clinical and Vaccine Immunology (2012) 19(7):1083-1092.

*Primary Examiner* — Rodney P Swartz
(74) *Attorney, Agent, or Firm* — David L. Marks; John D. Fado; Lesley Shaw

(57) ABSTRACT

Compositions of immunogenic proteins of *Mycobacterium avium* subspecies *paratuberculosis* (MAP) are effective for stimulating a protective immune response in animals against MAP. Combinations of MAP1087 with two or more of MAP1204, MAP1272c and MAP2077c are effective for stimulating a protective immune response in animals against MAP and can be administered as vaccines against *paratuberculosis* (Johne's disease). Induction of the immune response significantly reduces or eliminates colonization of the animal by MAP, and consequently reduces or eliminates the symptoms of clinical disease in animals infected with MAP and reduces or eliminates fecal shedding of MAP. Vaccination with the compositions provides protection against clinical disease and reduces transmission of MAP infection within a herd.

45 Claims, 22 Drawing Sheets

MLGYVLARIGQSAIVLLAVFSLVFWGVSILPADPAAIFVAKGEGYFNPDIVAQVKAFYGY
DRPLWVQYFAQLNQVLHGHFGFSLSSGQAVTDRIGGVIGETLKLAATATGFAVLFAVSVT
ALATTCAPVRSVLRAIPPLFGAVPTF

Figure 1A

MKIEEGKLVIWINGDKGYNGLAEVGKKFEKDTGIKVTVEHPDKLEEKFPQVAATGDGPDIIFWAHDRFGGYAQS
GLLAEITPDKAFQDKLYPFTWDAVRYNGKLIAYPIAVEALSLIYNKDLLPNPPKTWEEIPALDKELKAKGKSAL
MFNLQEPYFTWPLIAADGGYAFKYENGKYDIKDVGVDNAGAKAGLTFLVDLIKNKHMNADTDYSIAEAAFNKGE
TAMTINGPWAWSNIDTSKVNYGVTVLPTFKGQPSKPFVGVLSAGINAASPNKELAKEFLENYLLTDEGLEAVNK
DKPLGAVALKSYEEELAKDPRIAATMENAQKGEIMPNIPQMSAFWYAVRTAVINAASGRQTVDEALKDAQTNSS
SNNNNNNNNNNLGIEGRISEFGSSRMLGYVLARIGQSAIVLLAVFSLVFWGVSILPADPAAIFVAKGEGYFNPD
IVAQVKAFYGYDRPLWVQYFAQLNQVLHGHFGFSLSSGQAVTDRIGGVIGETLKLAATATGFAVLFAVSVTALA
TTCAPVRSVLRAIPPLFGAVPTF*

Figure 1B

MRRNRFRLIVFAWITAMVTGLMFSVAPTPAALADPGEWDPTLPAQISAGAPGDPLAVANA
SLQATAQATQTTLNLGKQFLGGLGINLGGNDAPAAAATPSNPGGKIPRVYGRQAIEYVIK
RMGSQMGVPYSWGGGSLDGPSKGVGDGANITGFDCSGLMRYGFAGVGVLIPRFSGDQYNA
GRHIPQDQARRGDLIFYGPGGSQHVTMYLGNGQMLEASGSAGKVTVSPVRKPGMTPFLTR
IIEY

Figure 2A

MKIEEGKLVIWINGDKGYNGLAEVGKKFEKDTGIKVTVEHPDKLEEKFPQVAATGDGPDIIFWAHDRFGGYAQS
GLLAEITPDKAFQDKLYPFTWDAVRYNGKLIAYPIAVEALSLIYNKDLLPNPPKTWEEIPALDKELKAKGKSAL
MFNLQEPYFTWPLIAADGGYAFKYENGKYDIKDVGVDNAGAKAGLTFLVDLIKNKHMNADTDYSIAEAAFNKGE
TAMTINGPWAWSNIDTSKVNYGVTVLPTFKGQPSKPFVGVLSAGINAASPNKELAKEFLENYLLTDEGLEAVNK
DKPLGAVALKSYEEELAKDPRIAATMENAQKGEIMPNIPQMSAFWYAVRTAVINAASGRQTVDEALKDAQTNSS
SNNNNNNNNNNLGIEGRISEFGSSRMRRNRFRLIVFAWITAMVTGLMFSVAPTPAALADPGEWDPTLPAQISAG
APGDPLAVANASLQATAQATQTTLNLGKQFLGGLGINLGGNDAPAAAATPSNPGGKIPRVYGRQAIEYVIKRMG
SQMGVPYSWGGGSLDGPSKGVGDGANITGFDCSGLMRYGFAGVGVLIPRFSGDQYNAGRHIPQDQARRGDLIFY
GPGGSQHVTMYLGNGQMLEASGSAGKVTVSPVRKPGMTPFLTRIIEY*

Figure 2B

```
VRSQRGGPRPVHEPGRTREVTAPRPDECRRGQERPGKMKRIYAFAIGLALLGAPAAPMVV
PPVATADPGVRAMDYQQATDVVIARGLSQRGVPFSWAGGGINGPTRGTGTGANTVGFDAS
GLMQYAYAGAGIKLPRSSGAMYRVGQKILPQQARKGDLIFYGPEGTQSVAMYLGNNQMLE
VGDVVQVSPVRTAGMAPYMVRVLGTTAPTQQVPQQAPLQQTPAQQAPLQQTPGQQAPLQQ
TPGQQLPTQQAPLQQVPGQQVPGQQLPTQQAPQQAPLQLAPTQQAPLQQLPTQQSPLQQL
PVQQSPLQPAGAGLTR
```

Figure 3A

```
MKIEEGKLVIWINGDKGYNGLAEVGKKFEKDTGIKVTVEHPDKLEEKFPQVAATGDGPDIIFWAHDRFGGYAQS
GLLAEITPDKAFQDKLYPFTWDAVRYNGKLIAYPIAVEALSLIYNKDLLPNPPKTWEEIPALDKELKAKGKSAL
MFNLQEPYFTWPLIAADGGYAFKYENGKYDIKDVGVDNAGAKAGLTFLVDLIKNKHMNADTDYSIAEAAFNKGE
TAMTINGPWAWSNIDTSKVNYGVTVLPTFKGQPSKPFVGVLSAGINAASPNKELAKEFLENYLLTDEGLEAVNK
DKPLGAVALKSYEEELAKDPRIAATMENAQKGEIMPNIPQMSAFWYAVRTAVINAASGRQTVDEALKDAQTNSS
SNNNNNNNNNNLGIEGRISEFGSSRVRSQRGGPRPVHEPGRTREVTAPRPDECRRGQERPGKMKRIYAFAIGLA
LLGAPAAPMVVPPVATADPGVRAMDYQQATDVVIARGLSQRGVPFSWAGGGINGPTRGTGTGANTVGFDASGLM
QYAYAGAGIKLPRSSGAMYRVGQKILPQQARKGDLIFYGPEGTQSVAMYLGNNQMLEVGDVVQVSPVRTAGMAP
YMVRVLGTTAPTQQVPQQAPLQQTPAQQAPLQQTPGQQAPLQQTPGQQLPTQQAPLQQVPGQQVPGQQLPTQQA
PQQAPLQLAPTQQAPLQQLPTQQSPLQQLPVQQSPLQPAGAGLTR*
```

Figure 3B

MVTPLTLDTGRGSDGNPVLVAVGEIDLSNIDAFHRALATATAEVTGSDGAVLVDLSAVEY
VDSAAINALAAHADHIALVAHPVLMPVFRVSGLTELTTVEAAPPPPAPR

Figure 4A

MKIEEGKLVIWINGDKGYNGLAEVGKKFEKDTGIKVTVEHPDKLEEKFPQVAATGDGPDIIFWAHDRFGGYAQS
GLLAEITPDKAFQDKLYPFTWDAVRYNGKLIAYPIAVEALSLIYNKDLLPNPPKTWEEIPALDKELKAKGKSAL
MFNLQEPYFTWPLIAADGGYAFKYENGKYDIKDVGVDNAGAKAGLTFLVDLIKNKHMNADTDYSIAEAAFNKGE
TAMTINGPWAWSNIDTSKVNYGVTVLPTFKGQPSKPFVGVLSAGINAASPNKELAKEFLENYLLTDEGLEAVNK
DKPLGAVALKSYEEELAKDPRIAATMENAQKGEIMPNIPQMSAFWYAVRTAVINAASGRQTVDEALKDAQTNSS
SNNNNNNNNNNLGIEGRISEFGSSRMVTPLTLDTGRGSDGNPVLVAVGEIDLSNIDAFHRALATATAEVTGSDG
AVLVDLSAVEYVDSAAINALAAHADHIALVAHPVLMPVFRVSGLTELTTVEAAPPPPAPR*

Figure 4B

```
ATGAAAATCGAAGAAGGTAAACTGGTAATCTGGATTAACGGCGATAAAGGCTATAACGGTCTCGCTGAAGTCGG
TAAGAAATTCGAGAAAGATACCGGAATTAAAGTCACCGTTGAGCATCCGGATAAACTGGAAGAGAAATTCCCAC
AGGTTGCGGCAACTGGCGATGGCCCTGACATTATCTTCTGGGCACACGACCGCTTTGGTGGCTACGCTCAATCT
GGCCTGTTGGCTGAAATCACCCCGGACAAAGCGTTCCAGGACAAGCTGTATCCGTTTACCTGGGATGCCGTACG
TTACAACGGCAAGCTGATTGCTTACCCGATCGCTGTTGAAGCGTTATCGCTGATTTATAACAAAGATCTGCTGC
CGAACCCGCCAAAAACCTGGGAAGAGATCCCGGCGCTGGATAAAGAACTGAAAGCGAAAGGTAAGAGCGCGCTG
ATGTTCAACCTGCAAGAACCGTACTTCACCTGGCCGCTGATTGCTGCTGACGGGGGTTATGCGTTCAAGTATGA
AAACGGCAAGTACGACATTAAAGACGTGGGCGTGGATAACGCTGGCGCGAAAGCGGGTCTGACCTTCCTGGTTG
ACCTGATTAAAAACAAACACATGAATGCAGACACCGATTACTCCATCGCAGAAGCTGCCTTTAATAAAGGCGAA
ACAGCGATGACCATCAACGGCCCGTGGGCATGGTCCAACATCGACACCAGCAAAGTGAATTATGGTGTAACGGT
ACTGCCGACCTTCAAGGGTCAACCATCCAAACCGTTCGTTGGCGTGCTGAGCGCAGGTATTAACGCCGCCAGTC
CGAACAAAGAGCTGGCAAAAGAGTTCCTCGAAAACTATCTGCTGACTGATGAAGGTCTGGAAGCGGTTAATAAA
GACAAACCGCTGGGTGCCGTAGCGCTGAAGTCTTACGAGGAAGAGTTGGCGAAAGATCCACGTATTGCCGCCAC
TATGGAAAACGCCCAGAAAGGTGAAATCATGCCGAACATCCCGCAGATGTCCGCTTTCTGGTATGCCGTGCGTA
CTGCGGTGATCAACGCCGCCAGCGGTCGTCAGACTGTCGATGAAGCCCTGAAAGACGCGCAGACTAATTCGAGC
TCGAACAACAACAACAATAACAATAACAACAACCTCGGGATCGAGGGAAGGATTTCAGAATTCGGATCCTCTAG
AATGCTCGGCTACGTTCTCGCCCGGATCGGCCAGTCGGCCATCGTGCTGCTGGCGGTCTTCAGCCTGGTGTTCT
GGGGCGTCAGCATCCTGCCGGCCGATCCGGCGGCGATCTTCGTGGCCAAGGGGGAGGGCTACTTCAACCCCGAC
ATCGTCGCGCAGGTCAAGGCGTTCTACGGCTACGACCGGCCGCTGTGGGTGCAGTACTTCGCGCAGCTGAACCA
GGTGCTGCACGGGCATTTCGGCTTCTCGCTGTCCAGCGGTCAGGCCGTCACCGACCGGATCGGCGGGGTGATCG
GCGAGACCCTGAAACTGGCGGCCACCGCCACCGGGTTCGCGGTGCTGTTCGCGGTGTCGGTCACCGCGCTGGCG
ACCACCTGCGCGCCGGTGCGGTCGGTGCTGCGCGCGATCCCGCCGCTGTTCGGCGCGGTCCCCACGTTTTGA
```

Figure 5

```
ATGAAAATCGAAGAAGGTAAACTGGTAATCTGGATTAACGGCGATAAAGGCTATAACGGTCTCGCTGAAGTCGG
TAAGAAATTCGAGAAAGATACCGGAATTAAAGTCACCGTTGAGCATCCGGATAAACTGGAAGAGAAATTCCCAC
AGGTTGCGGCAACTGGCGATGCCCTGACATTATCTTCTGGGCACACGACCGCTTTGGTGGCTACGCTCAATCT
GGCCTGTTGGCTGAAATCACCCCGGACAAAGCGTTCCAGGACAAGCTGTATCCGTTTACCTGGGATGCCGTACG
TTACAACGGCAAGCTGATTGCTTACCCGATCGCTGTTGAAGCGTTATCGCTGATTTATAACAAAGATCTGCTGC
CGAACCCGCCAAAAACCTGGGAAGAGATCCCGGCGCTGGATAAAGAACTGAAAGCGAAAGGTAAGAGCGCGCTG
ATGTTCAACCTGCAAGAACCGTACTTCACCTGGCCGCTGATTGCTGCTGACGGGGGTTATGCGTTCAAGTATGA
AAACGGCAAGTACGACATTAAAGACGTGGGCGTGGATAACGCTGGCGCGAAAGCGGGTCTGACCTTCCTGGTTG
ACCTGATTAAAAACAAACACATGAATGCAGACACCGATTACTCCATCGCAGAAGCTGCCTTTAATAAAGGCGAA
ACAGCGATGACCATCAACGGCCCGTGGGCATGGTCCAACATCGACACCAGCAAAGTGAATTATGGTGTAACGGT
ACTGCCGACCTTCAAGGGTCAACCATCCAAACCGTTCGTTGGCGTGCTGAGCGCAGGTATTAACGCCGCCAGTC
CGAACAAAGAGCTGGCAAAAGAGTTCCTCGAAAACTATCTGCTGACTGATGAAGGTCTGGAAGCGGTTAATAAA
GACAAACCGCTGGGTGCCGTAGCGCTGAAGTCTTACGAGGAAGAGTTGGCGAAAGATCCACGTATTGCCGCCAC
TATGGAAAACGCCCAGAAAGGTGAAATCATGCCGAACATCCCGCAGATGTCCGCTTTCTGGTATGCCGTGCGTA
CTGCGGTGATCAACGCCGCCAGCGGTCGTCAGACTGTCGATGAAGCCCTGAAAGACGCGCAGACTAATTCGAGC
TCGAACAACAACAACAATAACAATAACAACAACCTCGGGATCGAGGGAAGGATTTCAGAATTCGGATCCTCTAG
AATGCGCCGCAACCGGTTTCGTCTCATCGTCTTCGCCTGGATCACCGCCGATGGTGACCGGGCTGATGTTTTCCG
TGGCACCGACGCCGGCCGCGCTGGCCGACCCCGGCGAGTGGGATCCCACCCTGCCGGCCCAGATCAGTGCCGGC
GCCCCGGGCGATCCGCTCGCCGTCGCCAACGCCTCGCTGCAGGCCACCGCGCAGGCCACCCAGACCACGCTGAA
CCTGGGCAAGCAATTCCTCGGCGGGCTCGGCATCAACCTGGGCGGCAACGACGCGCCCGCGGCCGCGGCCACGC
CGTCCAACCCGGGCGGCAAGATCCCGCGGGTCTACGGCCGGCAGGCCATCGAGTACGTGATCAAGCGGATGGGG
TCGCAGATGGGGTGCCGTACTCGTGGGGCGGCGGCTCGGCTGGACGGTCCCAGCAAGGGTGTCGGCGACGGCGG
CAACATCACCGGGTTCGACTGCTCGGGCTGATGCGCTACGGCTTCGCCGGGGTCGGCGTGCTGATCCCGCGGT
TCTCCGGCGACCAGTACAACGCCGGGCGTCACATCCCGCAGGATCAGGCCCGCCGCGGCGACCTCATCTTCTAC
GGCCCGGGCGGGTCCCAGCACGTCACCATGTACCTGGGCAACGGGCAGATGCTCGAGGCGTCCGGCAGCGCCGG
CAAGGTCACCGTCAGCCCGGTGCGCAAGCCCGGCATGACACCGTTCCTGACTAGGATCATCGAGTACTGA
```

Figure 6

```
ATGAAAATCGAAGAAGGTAAACTGGTAATCTGGATTAACGGCGATAAAGGCTATAACGGTCTCGCTGAAGTCGG
TAAGAAATTCGAGAAAGATACCGGAATTAAAGTCACCGTTGAGCATCCGGATAAACTGGAAGAGAAATTCCCAC
AGGTTGCGGCAACTGGCGATGGCCCTGACATTATCTTCTGGGCACACGACCGCTTTGGTGGCTACGCTCAATCT
GGCCTGTTGGCTGAAATCACCCCGGACAAAGCGTTCCAGGACAAGCTGTATCCGTTTACCTGGGATGCCGTACG
TTACAACGGCAAGCTGATTGCTTACCCGATCGCTGTTGAAGCGTTATCGCTGATTTATAACAAAGATCTGCTGC
CGAACCCGCCAAAAACCTGGGAAGAGATCCCGGCGCTGGATAAAGAACTGAAAGCGAAAGGTAAGAGCGCGCTG
ATGTTCAACCTGCAAGAACCGTACTTCACCTGGCCGCTGATTGCTGCTGACGGGGGTTATGCGTTCAAGTATGA
AAACGGCAAGTACGACATTAAAGACGTGGGCGTGGATAACGCTGGCGCGAAAGCGGGTCTGACCTTCCTGGTTG
ACCTGATTAAAAACAAACACATGAATGCAGACACCGATTACTCCATCGCAGAAGCTGCCTTTAATAAAGGCGAA
ACAGCGATGACCATCAACGGCCCGTGGGCATGGTCCAACATCGACACCAGCAAAGTGAATTATGGTGTAACGGT
ACTGCCGACCTTCAAGGGTCAACCATCCAAACCGTTCGTTGGCGTGCTGAGCGCAGGTATTAACGCCGCCAGTC
CGAACAAAGAGCTGGCAAAAGAGTTCCTCGAAAACTATCTGCTGACTGATGAAGGTCTGGAAGCGGTTAATAAA
GACAAACCGCTGGGTGCCGTAGCGCTGAAGTCTTACGAGGAACAGTTGGCGAAAGATCCACGTATTGCCGCCAC
TATGGAAAACGCCCAGAAAGGTGAAATCATGCCGAACATCCCGCAGATGTCCGCTTTCTGGTATGCCGTGCGTA
CTGCGGTGATCAACGCCGCCAGCGGTCGTCAGACTGTCGATGAAGCCCTGAAAGACGCGCAGACTAATTCGAGC
TCGAACAACAACAACAATAACAATAACAACAACCTCGGGATCGAGGGAAGGATTTCAGAATTCGGATCCTCTAG
AGTGCGATCCCAGCGTGGGGGTCCTCGCCCGGTCCATGAACCGGGGCGGACGCGCGAGGTCACCGCGCCGAGGC
CCGACGAGTGCCGGAGAGGCCAGGAAAGCCCAGGAAAAATGAAACGCATCTACGCCTTCGCGATCGGTTTGGCC
CTACTCGGGGCGCCGGCGGCGCCGATGGTGGTTCCCCCGTCGCGACCGCCGACCCGGGCGTCAGGGCGATGGA
CTATCAGCAGGCCACCGACGTGGTGATCGCGCGCGGTCTGTCGCAGCGCGGTGTGCCGTTCTCCTGGGCCGGCG
GCGGCATCAACGGCCCCACCCGCGGCACCGGGACCGGCGCCAACACCGTCGGTTTCGACGCGTCCGGGCTGATG
CAGTACGCGTACGCCGGCGCCGGCATCAAGCTGCCGCGCTCGTCCGGCGCGATGTACCGCGTCGGCCAGAAGAT
CCTGCCGCAGCAGGCCCGCAAGGGTGACCTGATCTTCTACGGCCCCGAGGGCACCCAGAGCGTCGCAATGTACC
TGGGCAACAACCAGATGCTCGAGGTCGGCGACGTGGTGCAGGTGTCGCCGGTGCGTACCGCCGGCATGGCGCCC
TACATGGTCCGGGTGTTGGGACCACGGCGCCCACCCAGCAGGTTCCGCAGCAGGCCGCTGCAGCAGACCCC
GGCGCAGCAGGCGCCCTTGCAACAGACCCCGGGCCAGCAGGCGCCCTTGCAGCAGACCCCGGGCCAGCAACTGC
CCACCCAGCAGGCCCCGCTGCAACAGGTTCCGGGGCAGCAGGTTCCGGGGCAGCAGCTGCCCACCCAGCAAGCG
CCCCAGCAGGCACCCCTGCAGCTGGCGCCGACCCAGCAGGCGCCGCTGCAACAGCTGCCGACCCAGCAGTCACC
GCTGCAGCAGCTGCCGGTCCAGCAGTCGCCACTGCAGCCGGCGGGCGCCGGACTCACCCGGTAG
```

Figure 7

```
ATGAAAATCGAAGAAGGTAAACTGGTAATCTGGATTAACGGCGATAAAGGCTATAACGGTCTCGCTGAAGTCGG
TAAGAAATTCGAGAAAGATACCGGAATTAAAGTCACCGTTGAGCATCCGGATAAACTGGAAGAGAAATTCCCAC
AGGTTGCGGCAACTGGCGATGGCCCTGACATTATCTTCTGGGCACACGACCGCTTTGGTGGCTACGCTCAATCT
GGCCTGTTGGCTGAAATCACCCCGGACAAAGCGTTCCAGGACAAGCTGTATCCGTTTACCTGGGATGCCGTACG
TTACAACGGCAAGCTGATTGCTTACCCGATCGCTGTTGAAGCGTTATCGCTGATTTATAACAAAGATCTGCTGC
CGAACCCGCCAAAAACCTGGGAAGAGATCCCGGCGCTGGATAAAGAACTGAAAGCGAAAGGTAAGAGCGCGCTG
ATGTTCAACCTGCAAGAACCGTACTTCACCTGGCCGCTGATTGCTGCTGACGGGGGTTATGCGTTCAAGTATGA
AAACGGCAAGTACGACATTAAAGACGTGGGCGTGGATAACGCTGGCGCGAAAGCGGGTCTGACCTTCCTGGTTG
ACCTGATTAAAAACAAACACATGAATGCAGACACCGATTACTCCATCGCAGAAGCTGCCTTTAATAAAGGCGAA
ACAGCGATGACCATCAACGGCCCGTGGGCATGGTCCAACATCGACACCAGCAAAGTGAATTATGGTGTAACGGT
ACTGCCGACCTTCAAGGGTCAACCATCCAAACCGTTCGTTGGCGTGCTGAGCGCAGGTATTAACGCCGCCAGTC
CGAACAAAGAGCTGGCAAAAGAGTTCCTCGAAAACTATCTGCTGACTGATGAAGGTCTGGAAGCGGTTAATAAA
GACAAACCGCTGGGTGCCGTAGCGCTGAAGTCTTACGAGGAAGAGTTGGCGAAAGATCCACGTATTGCCGCCAC
TATGGAAAACGCCCAGAAAGGTGAAATCATGCCGAACATCCCGCAGATGTCCGCTTTCTGGTATGCCGTGCGTA
CTGCGGTGATCAACGCCGCCAGCGGTCGTCAGACTGTCGATGAAGCCCTGAAAGACGCGCAGACTAATTCGAGC
TCGAACAACAACAACAATAACAATAACAACAACCTCGGGATCGAGGGAAGGATTTCAGAATTCGGATCCTCTAG
AATGGTCACCCCGCTGACGCTGGACACCGGCCGTGGTAGCGACGGCAACCCGGTGCTGGTGGCAGTGGGCGAAA
TCGACCTGAGCAACATCGACGCATTCCACCGGGCGCTGGCCACCGCCACCGCGGAGGTCACCGGGAGTGACGGC
GCGGTGCTCGTCGACCTCAGCGCCGTGGAGTATGTGGACAGCGCCGCCATCAATGCGTTGGCCGCGCACGCCGA
CCACATCGCGCTCGTCGCGCACCCGGTCCTGATGCCCGTCTTCAGGGTCAGCGGTTTGACCGAGCTGACCACCG
TCGAAGCCGCACCCCCGCCGCCGGCGCCTCGTTGA
```

Figure 8

RECOMBINANT MYCOBACTERIUM AVIUM SUBSP. PARATUBERCULOSIS PROTEINS INDUCE IMMUNITY AND PROTECT AGAINST INFECTION

CROSS-REFERENCE TO RELATED APPLICATIONS

This application claims the benefit under 35 U.S.C. 1.19(e) of U.S. provisional 61/717,723, filed Oct. 24, 2012, the contents of which are incorporated by reference herein.

BACKGROUND OF THE INVENTION

1. Field of the Invention

The invention relates to compositions of proteins effective as vaccines to induce immunity and protect animals against infection by *Mycobacterium avium* subspecies *paratuberculosis*.

2. Background of the Invention

*Paratuberculosis* vaccine studies have demonstrated the induction of both cellular and humoral immune responses, however, it is widely accepted that vaccination will not prevent infection. Some benefits of vaccination include reduced fecal shedding of *Mycobacterium avium* subspecies *paratuberculosis* (MAP) and reduced clinical signs in infected animals, with evidence suggesting a reduction in the incidence of disease within herds or severity of disease for individual animals (Kalis et al. Use of long-term vaccination with a killed vaccine to prevent fecal shedding of *Mycobacterium avium* subsp. *paratuberculosis* in dairy herds. Am. J. Vet. Res. 2001. 62:270-4; Begg et al. Vaccination of sheep against *M. paratuberculosis*: immune parameters and protective efficacy. Vaccine. 2005. 23:4999-5008; and Juste et al. Significant reduction in bacterial shedding and improvement in milk production in dairy farms after the use of a new inactivated *paratuberculosis* vaccine in a field trial. BMC Res Notes. 2009. 2:233-9). The heat-killed whole cell vaccine that is approved for use in the US (Mycopar, Fort Dodge Animal Health) is not ideal because of potential adverse reactions, including severe inflammation and granuloma formation at the injection site. In addition, vaccination with whole cell vaccines has been shown to interfere with bovine tuberculosis skin testing and serologic detection of MAP infected animals (Köhler et al. Immune reactions in cattle after immunization with a *Mycobacterium paratuberculosis* vaccine and implications for the diagnosis of *M. paratuberculosis* and *M. bovis* infections. J Vet Med B. 2001. 48:185-95; Muskens et al. Evaluation of the long-term immune response in cattle after vaccination against *paratuberculosis* in two Dutch dairy herds. Vet. Microbiol. 2002. 86:269-78; and Nedrow et al. Antibody and skin-test responses of sheep vaccinated against Johne's disease. Vet Immunol Immunopathol. 116:109-12). Developing subunit or DNA vaccines would significantly reduce or eliminate some of the troubling aspects of the whole cell vaccine without sacrificing beneficial properties.

Several MAP proteins or protein complexes have demonstrated success for use as subunit vaccines, including a 70 kDa heat shock protein, a 74F polyprotein, and a mixture of Ag85/SOD proteins. Immunization with these protein or protein complexes has provided protection against MAP challenge in mice, cattle and goat models, resulting in reduced colonization of tissues and decreased shedding in the feces (Koets et al. Mycobacterial 70 kD heat-shock protein is an effective subunit vaccine against bovine *paratuberculosis*. Vaccine. 2006. 24:2550-9; Chen et al. Immune responses in mice to *Mycobacterium avium* subsp. *paratuberculosis* following vaccination with a novel 74F recombinant polyprotein. Vaccine. 2008. 26:1253-62; and Kathaperumal et al. Vaccination with recombinant *Mycobacterium avium* subsp. *paratuberculosis* proteins induces differential immune responses and protects calves against infection by oral challenge. Vaccine. 2008. 26:1652-63). Each of these subunit vaccines has demonstrated that they are able to induce both cell-mediated and humoral immune responses in the respective hosts, suggesting strong protective measures. Further, it was recently demonstrated that the Hsp70 subunit vaccine does not cross-react with the comparative cervical skin test, a diagnostic tool commonly used for bovine tuberculosis in the field (Santema et al. Heat shock protein 70 subunit vaccination against bovine *paratuberculosis* does not interfere with current immunodiagnostic assays for bovine tuberculosis. Vaccine. 2009. 27:2312-19). Positive responses to AvPPD were noted in all vaccinated animals, however, responses to BoPPD were demonstrated only for cattle vaccinated with whole cell vaccine (Gudair) and not for those vaccinated with Hsp70 (Santema et al. ibid), demonstrating that a subunit vaccine can be more discriminative for identification of animals infected or vaccinated against MAP versus those animals infected with *M. bovis*.

However, despite these advances, the need remains for improved vaccines for protecting animals against *paratuberculosis*.

SUMMARY OF THE INVENTION

We have now discovered compositions of immunogenic proteins of *Mycobacterium avium* subspecies *paratuberculosis* (MAP) which are effective for stimulating a protective immune response in animals against MAP. These immunogenic proteins from MAP include MAP1087, MAP1204, MAP1272c and MAP2077c. Combinations of MAP1087 with two or more of MAP1204, MAP1272c and MAP2077c are effective for stimulating a protective immune response in animals against MAP and can be administered as vaccines against *paratuberculosis* (Johne's disease). Induction of the immune response significantly reduces or eliminates colonization of the animal by MAP, and consequently reduces or eliminates the symptoms of clinical disease in animals infected with MAP and reduces or eliminates fecal shedding of MAP. Vaccination with the compositions provides protection against clinical disease and reduces transmission of MAP infection within a herd.

In accordance with this discovery, it is an object of this invention to provide a novel protective vaccine against MAP in animals.

Another object of this invention is to provide a novel vaccine which significantly reduces or eliminates colonization of the animal by MAP.

A further object of this invention is to provide a novel vaccine which provides protection to animals against clinical *paratuberculosis* and reduces transmission of MAP infection within a herd.

Other objects and advantages of this invention will become readily apparent from the ensuing description.

BRIEF DESCRIPTION OF THE DRAWINGS

FIG. 1A shows the amino acid sequence (SEQ ID NO: 1) of MAP1087, isolated from MAP and having a molecular weight of 15436 Daltons. FIG. 1B shows the amino acid sequence of recombinant fusion protein (SEQ ID NO: 5) of MAP1087 and maltose-binding protein (MBP) as cloned into and produced by *E. coli* as described in Example 1. The amino acids of the MAP1087 are underlined (amino acids 396-541 of FIG. 1B).

FIG. 2A shows the amino acid sequence (SEQ ID NO: 2) of MAP1204, isolated from MAP and having a molecular weight of 25415 Daltons. FIG. 2B shows the amino acid sequence of recombinant fusion protein (SEQ ID NO: 6) of MAP1204 and maltose-binding protein (MBP) as cloned into and produced by *E. coli* as described in Example 1. The amino acids of the MAP1204 are underlined (amino acids 396-639 of FIG. 2B).

FIG. 3A shows the amino acid sequence (SEQ ID NO: 3) of MAP1272c, isolated from MAP and having a molecular weight of 33404 Daltons. FIG. 3B shows the amino acid sequence of recombinant fusion protein (SEQ ID NO: 7) of MAP1272c and maltose-binding protein (MBP) as cloned into and produced by *E. coli* as described in Example 1. The amino acids of the MAP1272c are underlined (amino acids 396-711 of FIG. 3B).

FIG. 4A shows the amino acid sequence (SEQ ID NO: 4) of MAP2077c, isolated from MAP and having a molecular weight of 11074 Daltons. FIG. 4B shows the amino acid sequence of recombinant fusion protein (SEQ ID NO: 8) of MAP2077c and maltose-binding protein (MBP) as cloned into and produced by *E. coli* as described in Example 1. The amino acids of the MAP2077c are underlined (amino acids 396-504 of FIG. 4B).

FIG. 5 shows the MAP1087 nucleotide sequence (SEQ ID NO: 9) as cloned into the pMAL-c2 *E. coli* expression vector as described in Example 1. The underlined sequence (nucleotides 1186-1623) corresponds to the nucleotide sequence (Genome coordinates=1141173:1141613) of the cDNA from MAP encoding the isolated MAP1087 protein of FIG. 1A. Nucleotides 1-1185 correspond to the nucleotide sequence encoding the MBP fusion protein.

FIG. 6 shows the MAP1204 nucleotide sequence (SEQ ID NO: 10) as cloned into the pMAL-c2 *E. coli* expression vector as described in Example 1. The underlined sequence (nucleotides 1186-1917) corresponds to the nucleotide sequence (Genome coordinates=1265380:1266114) of the cDNA from MAP encoding the isolated MAP1204 protein of FIG. 2A. Nucleotides 1-1185 correspond to the nucleotide sequence encoding the MBP fusion protein.

FIG. 7 shows the MAP1272c nucleotide sequence (SEQ ID NO: 11) as cloned into the pMAL-c2 *E. coli* expression vector as described in Example 1. The underlined sequence (nucleotides 1186-2133) corresponds to the nucleotide sequence (Genome coordinates=1359174:1360124) of the cDNA from MAP encoding the isolated MAP1272c protein of FIG. 3A. Nucleotides 1-1185 correspond to the nucleotide sequence encoding the MBP fusion protein.

FIG. 8 shows the MAP2077c nucleotide sequence (SEQ ID NO: 12) as cloned into the pMAL-c2 *E. coli* expression vector as described in Example 1. The underlined sequence (nucleotides 1186-1512) corresponds to the nucleotide sequence (Genome coordinates=2285918:2286247) of the cDNA from MAP encoding the isolated MAP2077c protein of FIG. 4A. Nucleotides 1-1185 correspond to the nucleotide sequence encoding the MBP fusion protein.

DEFINITIONS

Figure 9:
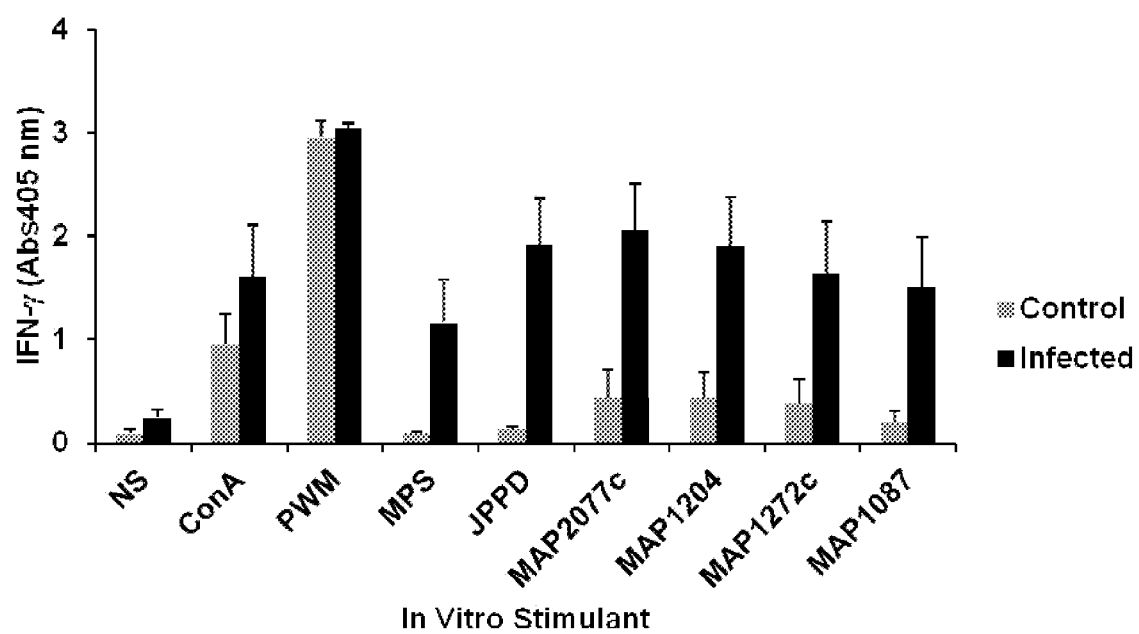
FIG. 9 shows the secretion of interferon-γ (ng/ml; IFN-γ) in Example 2 by control non-infected cows and cows naturally infected with *Mycobacterium avium* subsp. *paratuberculosis* upon incubation of whole blood with medium alone (NS); concanavalinA (ConA); pokeweed mitogen (PWM); a whole-cell sonicate of *Mycobacterium avium* subsp. *paratuberculosis* (MPS); johnin purified protein derivative (JPPD); and MAP proteins (2077c, 1204, 1272c, and 1087). Data are expressed as means±SEM. Significant differences between control and infection cows within in vitro treatment group are represented by asterisks (**P<0.01; *P<0.05).
Figure 10A:
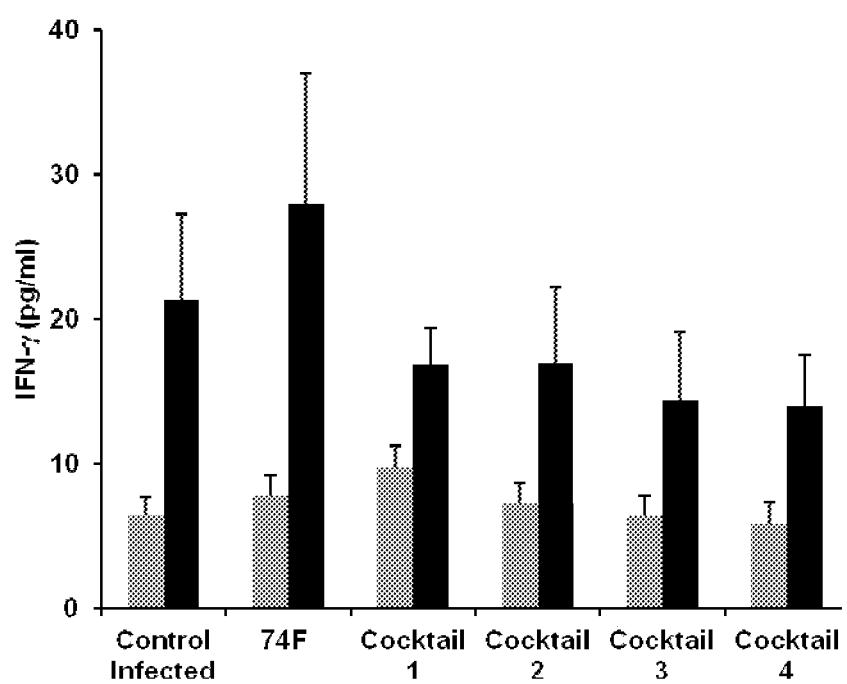
FIG. 10 shows the secretion of Th1-mediated cytokines, interferon-γ (A; IFN-γ, pg/ml) and interleukin-12 (B; IL-12, pg/ml), and Th2-mediated cytokines, interleukin-4 (C; IL-4, pg/ml), and interleukin-10 (D; IL-10; pg/ml) in Example 2 by splenocytes stimulated with medium alone (NS) or with a whole cell sonicate of *Mycobacterium avium* subsp. *paratuberculosis* (MPS). Splenocytes were isolated after 3 months of infection from control mice and mice vaccinated with 74F polyprotein or MAP protein cocktails 1-4. Data are expressed as means±SEM. Significant differences between NS and MPS within treatment group are represented by asterisks (**P<0.01; *P<0.05).
Figure 10B:
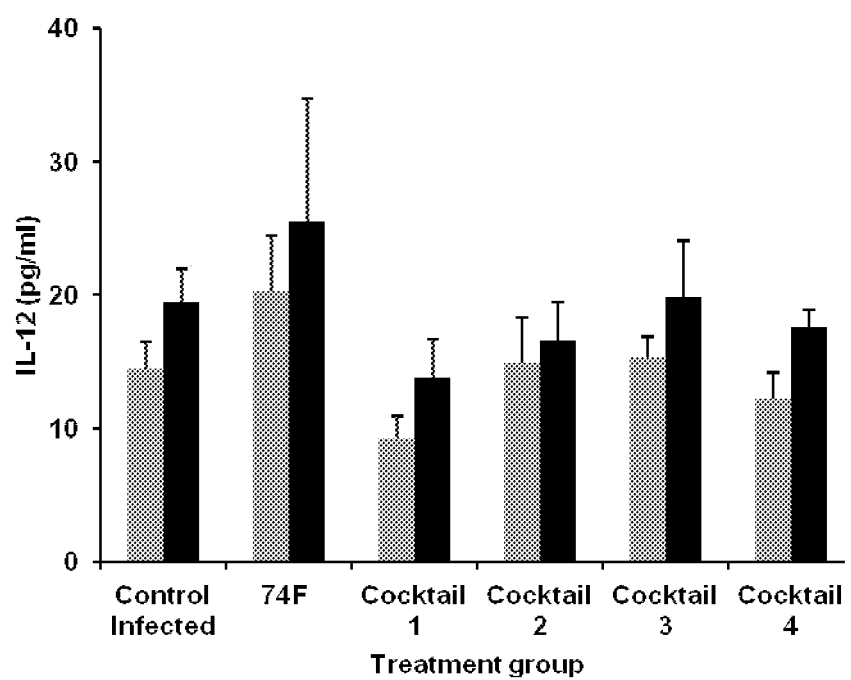
Figure 10C:
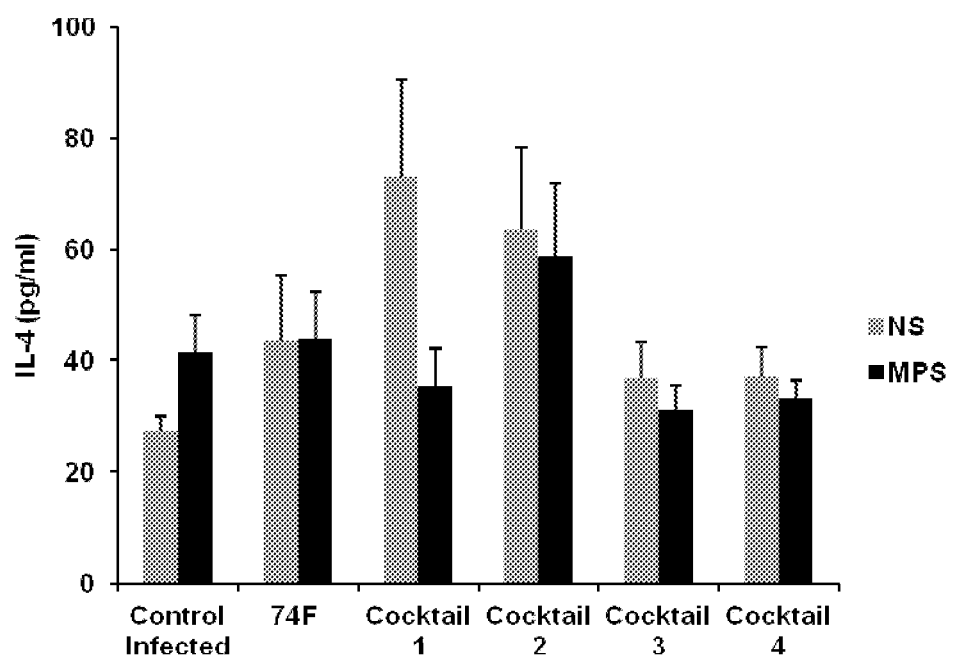
Figure 10D:
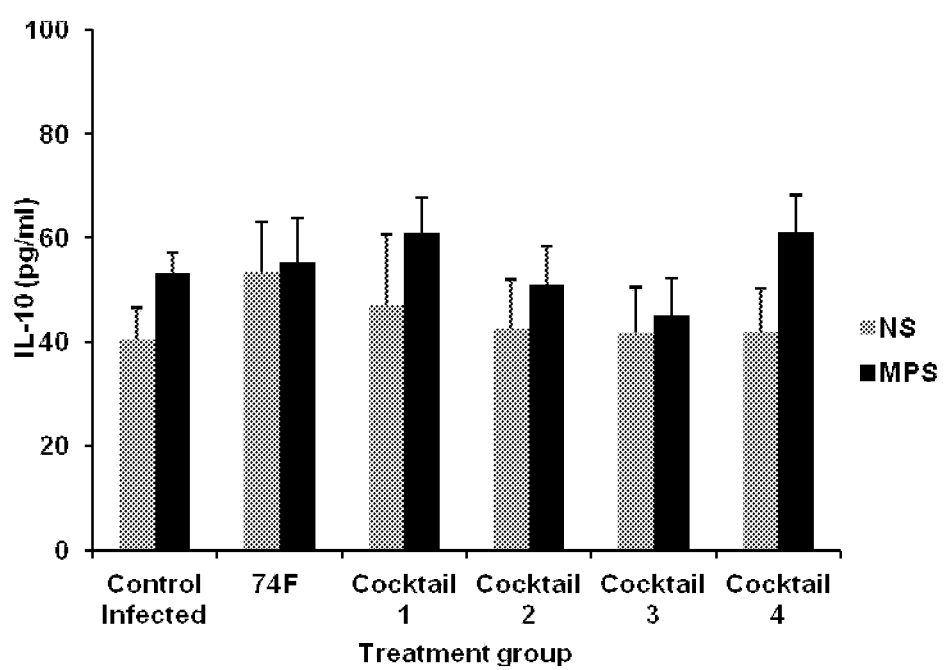

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as it occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, prokaryotic sequences and cDNA from eukaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase, which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In prokaryotes and some fungi, for example, the exogenous DNA may be maintained on an episomal element such as a plasmid. With respect to most eukaryotic cells, a stably transformed cell is one in which the exogenous DNA has been integrated into a chromosome so that it is inherited by daughter cells through chromosome replication. This stability is demonstrated by the ability of the eukaryotic cell to establish cell lines or clones comprised of a population of daughter cells containing the exogenous DNA.

Transcription. The process of producing mRNA from a structural gene.

Translation. The process of producing a polypeptide from mRNA.

Vaccine. Vaccine is defined herein in its broad sense to refer to any type of biological agent in an administrable form capable of stimulating a protective immune response in an animal inoculated with the vaccine. For purposes of this invention, the vaccine may comprise combinations of three or more of the immunogenic (antigenic) proteins MAP1087, MAP1204, MAP1272c and MAP2077c.

DETAILED DESCRIPTION OF THE INVENTION

In the following description, the nomenclature used to define the proteins and peptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

We have discovered that compositions of immunogenic proteins MAP1087, MAP1204, MAP1272c and MAP2077c of MAP are effective for stimulating an immune response in animals against MAP. Moreover, combinations or cocktails of MAP1087 with any two or all of MAP1204, MAP1272c and MAP2077c are particularly effective for stimulating a protective immune response in animals against MAP and can be administered as vaccines against *paratuberculosis* (Johne's disease). The proteins have been isolated, substantially free from other proteins or cell components which are normally present in the cells of MAP, such that the MAP1087, MAP1204, MAP1272c and MAP2077c proteins are the only significant protein(s) or peptide(s) in the sample and may be used effectively as a vaccine. Moreover, all of the proteins have been produced in recombinant form as described herein below. The term "isolated" encompasses not only proteins which have been recovered from naturally occurring cells, but also recombinant proteins and synthesized proteins. Compositions of the MAP1087, MAP1204, MAP1272c and MAP2077c proteins, including recombinants, are immunogenic, effective for eliciting a protective immune response against MAP, which response is mediated by humoral, i.e., antibodies, and/or cellular processes. Each of MAP1087, MAP1204, MAP1272c and MAP2077c has been previously described, including their amino acid sequences are corresponding gene sequences. However, their use as a vaccine has not been described.

The isolated MAP1087, MAP1204, MAP1272c and MAP2077c have been sequenced, and their amino acid sequences are shown in FIGS. 1A, 2A, 3A and 4A, and correspond to SEQ ID NOs: 1-4, respectively. MAP1087 is an ABC transporter permease protein with a calculated molecular weight of 15.4 kDa, MAP1204 and MAP1272c are putative invasion proteins of the NipC/P60 family having calculated molecular weights of 25.4 and 33.4 kDa, respectively, and MAP2077c is an STAS domain containing protein having a calculated molecular weight of 11.1 kDa. Moreover, when utilizing recombinant proteins, the proteins may be modified to assist cloning in the selected vector and/or their separation and recovery, and the expressed proteins may further include optional, additional terminal amino acid sequences (not of MAP origin). For example, FIGS. 1B, 2B, 3B and 4B show the amino acid sequences (SEQ ID NOs: 5-8) of the MAP1087, MAP1204, MAP1272c and MAP2077c fusion proteins as cloned into and produced by the *E. coli* expression vector as described in Example 1. The underlined sequence of FIGS. 1B, 2B, 3B and 4B correspond to the amino acid sequences of FIGS. 1A, 2A, 3A and 4A. The N-terminal amino acids which are not underlined (amino acids 1-395) correspond to the MBP fusion protein. It is also understood that invention encompasses substantial equivalents of the MAP1087, MAP1204, MAP1272c and MAP2077c proteins which retain the ability to elicit an immune response in an animal against MAP. The practitioner of ordinary skill in the art will recognize that slight deviations of the amino acid sequences may be made without significantly affecting the efficacy of the proteins. Substantial equivalents of the MAP1087, MAP1204, MAP1272c and MAP2077c proteins include conservative substitutions of amino acids with other amino acids, including either naturally occurring or non-conventional amino acids, which maintain substantially the same charge and hydrophobicity as the original amino acid. Conservative substitutions include for example, replacement of glycine for alanine, valine for isoleucine, leucine for isoleucine, aspartic acid for glutamic acid, lysine for arginine, asparagine for glutamine, phenylalanine for tryptophan, and tryptophan for tyrosine. Examples of conservative substitutions with non-conventional amino acids are described in Rosenberg et al. (U.S. Pat. No. 5,679,782) the contents of which are incorporated by reference herein.

The MAP1087, MAP1204, MAP1272c and MAP2077c proteins may be produced for use in accordance with this invention by a variety of techniques, including production of recombinant proteins, isolation from cells of MAP, and chemical synthesis. For example, it is envisioned that the MAP1087, MAP1204, MAP1272c and MAP2077c proteins may be synthesized by methods well known to those skilled in the art of peptide synthesis, such as exclusively solid-phase techniques, partial solid-phase techniques, fragment condensation, or classical solution addition. Without being limited thereto, suitable solution phase synthesis methods are described by Finn and Hoffman [In "Proteins," Vol. 2, 3rd Ed., H. Neurath and R. L. Hill (eds.), Academic Press, New York, pp. 105-253 (1976)], while solid phase synthesis methods are described by Barany and Merrifield [In "The Peptides," Vol. 2, E. Gross and J. Meienhofer (eds.), Academic Press, New York, pp. 3-284 (1979)], and stepwise solid phase synthesis methods are described by Merrifield [J. Am. Chem. Soc. 85: 2149-2154 (1963)], the contents of each of which are incorporated herein by reference. However, the proteins are preferably produced by recombinant DNA techniques, which are particularly suitable for large-scale use.

Recombinant MAP1087, MAP1204, MAP1272c and MAP2077c proteins may be obtained by transforming a microorganism using an expression vector including a promoter or operator, or both, together with one or more of the MAP1087, MAP1204, MAP1272c and MAP2077c encoding genes and causing such transformed microorganisms to express the proteins. The genes encoding each of the MAP1087, MAP1204, MAP1272c and MAP2077c proteins have been previously described, and the nucleic acid sequences of the cDNA encoding these proteins are available in GenBank as GeneID nos. 2719512, 2720812, 2720835 and 2719950, respectively. The nucleic acid sequences of the cDNA encoding the MAP1087, MAP1204, MAP1272c and MAP2077c proteins are also provided in FIGS. 5-8 (SEQ ID NOs. 9-12), respectively, each indicated by underlining. Specifically, the nucleic acid sequence of the cDNA encoding MAP1087 corresponds to nucleotides 1186-1623 of SEQ ID NO: 9 (FIG. 5); the nucleic acid sequence of the cDNA encoding MAP1204 corresponds to nucleotides 1186-1917 of SEQ ID NO: 10 (FIG. 6); the nucleic acid sequence of the cDNA encoding MAP1272c corresponds to nucleotides 1186-2133 of SEQ ID NO: 11 (FIG. 7); the nucleic acid sequence of the cDNA encoding MAP2077c corresponds to nucleotides 1186-1512 of SEQ ID NO: 12 (FIG. 8). Each of these sequences also include the optional nucleotide sequence encoding the MBP fusion protein, which corresponds to nucleotides 1-1185 of each of SEQ ID NOs: 9-12.

The DNA sequences encoding the MAP1087, MAP1204, MAP1272c and MAP2077c proteins can be used to prepare recombinant DNA molecules by cloning into any suitable vector. A variety of vector-host cell expression systems may be employed in practicing the present invention. *E. coli*, such as described in Example 1 hereinbelow, is particularly preferred. However, the novel invention described here can be applied with numerous hosts that would be desirable. Host strains may be of bacterial, fungal, or yeast origin. Ascertaining the most appropriate host-vector system is within the skill of the person in the art.

Vectors used in practicing the present invention are selected to be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof, such as those described in Maniatis et al. [Molecular Cloning: A Laboratory Manual, Cold Springs Harbor Laboratory, 1989] or Ausubel et al. [Current Protocols in Molecular Biology, John Wiley & Sons, Inc, 1995], the contents of each of which are herein incorporated by reference. Further, the vectors may be non-fusion vectors (i.e., those producing the protein of the invention not fused to any heterologous polypeptide), or alternatively, fusion vectors (i.e., those producing the protein fused to a vector encoded polypeptide). The fusion proteins would of course vary with the particular vector chosen. In accordance with a preferred embodiment, the vector is the pMAL-c2 expression vector (New England Biolabs, Beverly, Mass.) as described in the Examples.

Regardless of the specific vector utilized, various sites may be selected for insertion of the isolated DNA sequences. These sites are usually designated by the restriction enzyme or endonuclease that cuts them. The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

Each nucleotide sequence comprising the MAP1087, MAP1204, MAP1272c and MAP2077c encoding gene may be inserted into the desired vector by known techniques. If, however, the vector is to serve as an expression vector, the vector should have a promoter, and the DNA sequences should be inserted in the vector downstream of the promoter and operationally associated therewith (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eucaryotic). Alternatively, any or all of the above control sequences may be ligated to the coding sequence prior to insertion into the vector.

DNA constructs may be introduced into the appropriate host by numerous methods described in the technical and scientific literature. Transformation of bacteria or yeast may be performed using standard techniques described in Maniatis et al., supra. Techniques for transforming filamentous fungi may include those described by Goosen et al. [Handbook for Applied Mycology, Arora, Elander & Mukerji, eds. (1992) pp. 151-195] and May et al. [Applied Molecular Genetics of Filamentous Fungi, Kinghorn and Turner, eds. (1992) pp. 1-27]. Transformation with E. coli is described in the Examples.

In general, linear or circular DNA constructs may be introduced into the host by techniques utilizing protoplast fusion, polyethylene glycol, liposomes, lithium acetate, electroporation, physical damage, biolistic bombardment, or Agrobacterium mediated transformation.

Successful transformants may be isolated by using markers, contained on the expression vectors, which confer a selectable trait to the transformed host. These may include nutritional selection related to substrate utilization (such as, growth on acetamide containing medium) or prototrophy of a required growth product (such as, arginine, leucine, or uracil). Dominant selectable markers (such as, resistance to ampicillin, G418, hygromycin, and phleomycin) are also useful in selecting transformants that have taken up the introduced DNA construct.

The DNA construct may be replicated autonomously or integrated into the genome of the host. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

For use in animal vaccinations, the combinations or cocktails of the isolated MAP1087, MAP1204, MAP1272c and MAP2077c proteins will typically be formulated in conjunction with a suitable pharmaceutically acceptable carrier or diluent. Specifically, combinations of MAP1087 with two or more of MAP1204, MAP1272c and MAP2077c are effective for stimulating a protective immune response in animals against MAP and can be administered as vaccines against paratuberculosis (Johne's disease). As illustrated in the Examples, cocktails comprising the combinations: (1) MAP1087, MAP1204 and MAP1272c, (2) MAP1087, MAP1204 and MAP2077c, (3) MAP1087, MAP1272c and MAP2077c, as well as (4) all of MAP1087, MAP1204, MAP1272c and MAP2077c, are all effective. The proteins in the vaccine compositions are provided in an immunologically effective amount or dosage to the animal. As used herein, an "effective amount" is defined as that amount of the proteins which will elicit a protective immune response against subsequent challenge to virulent MAP, which may include either or both of antibody production against the proteins or a cell-mediated immune response against MAP, in a treated animal in comparison to an untreated control animal. In a preferred embodiment, induction of a protective immune response (including complete or partial immunity) may be demonstrated by one or more of: a significant reduction in MAP shedding, a significant reduction in the average MAP concentration in animal tissues (including but not limited to the ileum, liver and/or lymph nodes), a significant reduction in the duration of MAP colonization, or a significant reduction in the percentage of animals colonized with MAP, all in a population of vaccinated animals as compared to an unvaccinated control group (measured at a confidence level of at least 80%, preferably measured at a confidence level of 95%). The actual effective amount will vary with the route of administration, the target animal to be treated and its age and size, and may be readily determined empirically by the practitioner skilled in the art by routine antigen dose-response testing. By way of example and without being limited thereto, when treating bovine by intramuscular, subcutaneous or IV injection, it is envisioned that typical doses of the vaccine per animal will contain between approximately 0.1 to 0.5 mg of each MAP protein in the cocktail. For smaller and/or younger animals, it is envisioned that effective doses may be significantly reduced, with amounts of total protein as low as 0.1 mg being suitable. Although greater amounts of proteins may be administered, use of such higher levels is generally considered impractical. Dosage volumes may also vary, but will typically range between approximately 0.1 mL to 1 mL.

A variety of carriers or diluents are suitable for formulation with the MAP1087, MAP1204, MAP1272c and MAP2077c proteins. Such carriers or diluents include, but are not limited to, physiological saline, mineral oil, vegetable oils, aqueous carboxymethyl cellulose or polyvinylpyrrolidone. The skilled practitioner will recognize that such carriers should of course be compatible with the proteins. Phosphate buffered saline (PBS) is preferred. The vaccine formulations may also contain optional adjuvants, antibacterial agents or other pharmaceutically active agents as are known in the art. Suitable adjuvants for use herein will be effective for enhancing the immune response of the treated animal to the MAP protein immunogens of the vaccine. Preferred adjuvants include: dimethyl dioctadecylammonium bromide (DDA) in PBS, and the Sigma adjuvant system [i.e., containing 0.5 mg Monophosphoryl Lipid A (MPL; isolated from *Salmonella minnesota*) and 0.5 mg synthetic trehalose dicorynomycolate (an analogue of trehalose dimycolate from the cord factor of the tubercle *bacillus*) in 44 µL of squalene oil, 0.2% TWEEN 80 and water]. Other suitable adjuvants include but are not limited to mineral oil, vegetable oils, alum, aluminum hydroxide gel and alum, alum plus MPL, water in oil emulsions (such as Suprimm available through Novartis), Freund's incomplete adjuvant, Freund's incomplete adjuvant, and microparticles or nanoparticles or beads of biocompatible matrix materials such as (although not limited to) agar or polyacrylate. The amount of adjuvant will vary considerably with the particular adjuvant selected. By way of example, suitable amounts of DDA may vary between approximately 0.25 to 20 mg per dose in bovine, with 0.5 mg being preferred in calves. Other known immunogenic agents used in conventional vaccines for the target animals may also be included in the formulation.

The vaccines may be used for the treatment of any animal susceptible to infection by MAP. However, without being limited thereto, the vaccine is preferably used for the treatment of ruminant animals in the families Bovidae and Cervidae, particularly in meat and dairy animals of the Bovidae family, especially bovine (cattle), bison, caprine (goats), ovine (sheep) and the like. It is also envisioned that the vaccines may be used for the treatment of susceptible species that are traditionally free-ranging, but are subject to wildlife management practices. Examples of such species are reindeer, deer, antelope, elk, etc., and also exotic animals that are maintained in zoos and wildlife parks.

The vaccines may be effectively administered to an animal at any age. The vaccine is preferably administered to neonatal animals, but may also be administered to older animals after they attain immunocompetence. The vaccines may be administered to the subject animal by any convenient route which enables an immune response. However, parenteral injection (e.g., subcutaneous, intravenous, or intramuscular) is preferred, with subcutaneous injection being particularly preferred. The vaccine products could also be administered using a needle-less device. The vaccine may be administered in a single dose or in a plurality of doses. Dependent upon rearing conditions, the vaccine may be administered in multiple doses, the timing of which may be readily determined by the skilled artisan. By way of example, for treatment of bovine, boost vaccinations are preferably administered approximately 2-3 weeks after the initial vaccination.

The following examples are intended only to further illustrate the invention and are not intended to limit the scope of the invention which is defined by the claims.

Example 1

Recombinant MAP10897, MAP1204, MAP1272c and MAP2077c proteins were produced using the general techniques described by Bannantine and Paustian (Identification of diagnostic proteins in *Mycobacterium avium* subspecies *paratuberculosis* by a whole genome analysis approach. Methods Mol Biol. 2006. 345:185-96), the contents of which are incorporated by reference herein. In brief, each of the cDNA sequences encoding MAP10897, MAP1204, MAP1272c and MAP2077c fusion proteins as shown in FIGS. 5-8 were cloned into pMAL-c2 *E. coli* expression vectors (New England Biolabs, USA). The MAP were expressed as fusion proteins with maltose binding protein (MBP) vectors to aid expression and protein recovery. The cDNA sequences and vectors were digested with XbaI and HindIII restriction enzymes, and the digested DNA ligated into the vector. *E. coli* DH5-α cells were transformed with the ligated expression vectors. *E. coli* harboring the expression plasmids were cultured by rotary shaking at 37° C. in I L of LB media supplemented with glucose (0.2%) and ampicillin (100 mg/ml) and induced with 300 µL IPTG when the O.D.600 nm measured between 0.4-0.6. After a 2-hr induction at 37° C., cells were harvested by centrifugation. A lysate of the harvested cells was prepared by freeze-thaw cycles followed by brief sonication. The heterologously expressed MAP/MBP fusion proteins were then affinity purified from the *E. coli* lysates using amylose resin column chromatography. The MAP/MBP fusion proteins were eluted with column buffer containing 10 mM maltose and recovered.

Example 2

Materials and Methods

Antigen Screening

Four MAP proteins were evaluated for reactivity with control noninfected, subclinically and clinically infected cattle in a whole blood interferon-γ (IFN-γ) assay. Infection status of cattle was confirmed by bacteriologic culture for the fecal shedding of MAP and serologic assays by standard methods (Stabel. An improved method for cultivation of *Mycobacterium paratuberculosis* from bovine fecal samples and comparison to three other methods. J Vet Diagn Invest. 1997. 9:375-80; and Stabel et al. Mediation of host immune responses after immunization of neonatal calves with a heat-killed *Mycobacterium avium* subsp. *paratuberculosis* vaccine. Clin Vaccine Immunol. 2011. 2079-89). Whole blood was incubated with medium only (nonstimulated; NS); concanavalin A (ConA, Sigma); pokeweed mitogen (PWM; 10 µg/ml; Sigma); johnin purified protein derivative (JPPD; 10 µg/ml; National Veterinary Services Laboratory, Ames, Iowa), a whole-cell sonicate of MAP (MPS; 10 µg/ml; NADC), and one of the following MAP proteins, MAP1087, MAP1204, MAP1272c, MAP2077c, (10 µg/ml). After incubation at 39° C. for 18 hr, plasma was assayed using a Bovigam IFN-γ assay (Prionics, La Vista, Nebr.). The selection of the 4 MAP proteins, MAP1087, MAP1204, MAP1272c, and MAP2077c, used in the present study was based upon their immunogenic potential as defined by robust antigen-specific IFN-γ and antibody responses in infected cattle and negligible responses in noninfected control cows. These 4 proteins were arrayed in 4 cocktails containing 3 of the 4 proteins as follows: cocktail 1: MAP1087, MAP1204, MAP1272c; cocktail 2: MAP1087, MAP1204, MAP2077c; cocktail 3: MAP 1087, 1272c, 2077c; and cocktail 4: MAP1204, MAP1272c, 2077c.

Protein Expression and Purification

The four annotated coding sequences of the proteins were selected from a battery of recombinant proteins amplified from strain K-10 genomic DNA. The four proteins, MAP1087, MAP1204, MAP1272c, and MAP2077c, were expressed and purified as described in Example 1. 74F polyprotein, consisting of a combination of MAP1519 and MAP3527 peptides, was constructed as previously described (Chen et al. ibid). The 74F polyprotein had previously demonstrated efficacy in the mouse model as a vaccine for *paratuberculosis* (Chen et al. ibid).

Bacterial Strain

MAP used as the challenge strain was isolated from the ileum of clinical cow 167 (NADC) and was grown in Middlebrook 7H9 liquid medium (pH 5.9) supplemented with 0.5% Tween 80 (Sigma), 2 mg/ml mycobactin J (Allied Monitor Inc., Fayette, Mo.) and 10% oleic acid-albumin-dextrose complex (BD Biosciences, Franklin Lakes, N.J.). The final concentration of the bacteria was adjusted to $10^9$ cfu/ml and confirmed by serial dilution onto agar slants of Herrold's egg yolk medium (HEYM; BD) containing 2 mg/liter of mycobactin J (Allied Monitor) with a final read-out after 12 weeks of incubation. The presence of each of the 4 MAP proteins in the cocktails was confirmed in this strain by PCR and Western blot (data not shown). Clinical cow strain 167 was used as the challenge strain as it was expanded from a primary isolate from ileal tissue of a highly infected cow and had not been subjected to repeated passage in laboratory medium.

Mice

Six-week old, male Balb/c mice used in the study (Jackson Labs, Bar Harbor, Me.) were housed in biosecurity level-2 containment in disposable plastic cages with free access to water and standard mouse chow. All procedures were approved by the NADC Animal Care and Use Committee.

MAP Vaccines

Mice were randomly assigned to 7 treatment groups containing 10 mice each as follows: control uninfected (no vaccine, no MAP), control infected (no vaccine, MAP infection), 74F protein only (74F vaccine, MAP infection), cocktail 1 (cocktail 1, MAP infection), cocktail 2 (cocktail 2, MAP infection), cocktail 3 (cocktail 3, MAP infection) and cocktail 4 (cocktail 4, MAP infection). The 74F group received 50 µg total protein as described in a previous study (Chen et al. ibid) and mice in cocktail 1-4 groups were given 100 µg total protein in 100 µl volume per mouse subcutaneously (SQ) in the dorsal region. The control uninfected and control infected groups received 100 µl PBS as sham injections. Mice within each treatment group were boosted with the identical vaccine three weeks after the initial immunization. Two weeks after boosting, mice were inoculated intraperitoneally with live, virulent MAP strain 167 ($10^8$ in 100 µl). Three months after infection, mice were anesthetized by inhalation of isoflurane and decapitated with a guillotine. The liver, spleen, ileum and mesenteric lymph node were removed from each mouse, weighed, and processed for tissue culture as previously described (Huntley et al. Expression library immunization confers protection against *Mycobacterium avium* subsp. *paratuberculosis* infection. Infect Immun. 2005. 73:6877-84). Splenocytes were isolated from a portion of the spleen and cultured at $2.0 \times 10^6$ cells/ml with medium only (NS); ConA, 10 µg/ml; PWM, 10 µg/ml; and MPS, 10 µg/ml. Quantitative cytokine analyses was performed on 24 hr supernatants for interleukins (IL)-2, IL-4, IL-10, IL-12, IL-23 and IFN-γ using commercial ELISA kits, according to accompanying protocol (R & D Systems, Minneapolis, Minn.). After 6 days of incubation, splenocytes were harvested for flow cytometric analyses of CD3, CD4, γδ T cells (BD Biosciences), CD8, B cells, monocytes, CD44, CD62L, and CD25 expression (BioLegend, San Diego, Calif.). Data analyses were performed using FlowJo software (TreeStar, Inc., San Carlos, Calif.).

Antigen-specific $IgG_1$ and $IgG_{2a}$ responses were measured in mouse sera by ELISA. Briefly, plates (Nunc MaxiSorp module, Nunc, Roskilde, Denmark) were coated with 200 ng/well of a whole cell sonicate preparation of MAP (clinical strain 167, NADC) and incubated at 4° C. overnight. After blocking (1% BSA in TBST), diluted sera were added to the wells and incubated at 25° C. for 1 hr, followed by incubation with either horseradish peroxidase-conjugated goat anti-mouse $IgG_1$ or $IgG_{2a}$ (Kamiya Biochemical Co., Seattle, Wash.) for 20 min, and 3,3',5,5'-tetramethylbenzidine substrate solution (TMB; Kamiya Biomedical Co.) for 10 min. Absorbance at 450 nm was measured in a Victor $X_3$ Microplate reader (Perkin-Elmer, Shelton, Conn.).

Statistical Analysis

Data were analyzed using PROC MIXED procedure of the Statistical Analysis System (SAS Inst., Inc., Cary, N.C.). The model included the fixed effects of treatment (vaccination), stimulation (in vitro treatment), and treatment×stimulation interaction. When significant effects (P<0.05) due to treatment, stimulation, or treatment×stimulation interactions were detected, means separation was conducted by the Student's t test option in SAS. Designation of statistical significance within figures is described in each figure legend. Broad measures of statistical significance due to treatment or treatment×stimulation interactions may only be denoted within the text of the manuscript.

Results

Immugenicity of MAP Protein Candidates

The MAP proteins (MAP1087, MAP1204, MAP1272c, and MAP2077c) used in the present study to formulate vaccine cocktails demonstrated strong immunogenic potential, producing antigen-specific IFN-γ responses similar to or greater than the whole-cell sonicate of MAP (MPS) in Johne's subclinical and clinical cows (FIG. 9).

Cytokine Results

Results for Th1 and Th2-mediated cytokine secretion from splenocytes stimulated with either medium alone (NS) or with MPS are presented in FIG. 10. Stimulation of cells with MPS resulted in an upregulation (P<0.05) of IFN-γ compared to NS cultures in all infected groups. Vaccination with MAP protein cocktails reduced IFN-γ responses to MPS overall when compared to the control infected and 74F treatment groups (P<0.05). Secretion of IL-12 followed a similar trend with greater responses noted for the control infected and 74F groups compared to the protein cocktail vaccinates (FIG. 10B). MPS-stimulated splenocytes had greater (P<0.05) IL-4 responses compared to NS cultures only in control infected mice (FIG. 10C). Interestingly, immunization with MAP protein cocktails resulted in increased (P<0.05) IL-4 secretion in NS cultures for mice immunized with cocktails 1 and 2 compared to control infected mice. There were no significant effects due to vaccination on the secretion of IL-10, regardless of in vitro stimulation, however, (P<0.05) differences between NS and MPS-stimulated cultures were observed for control infected mice (FIG. 10D). Secretion of IL-2 and IL-23 were not influenced by vaccination but an upregulation of IL-23 was observed by stimulation of splenocytes with MPS in all infected mice (data not shown).

T Cell Populations

Figure 11A:
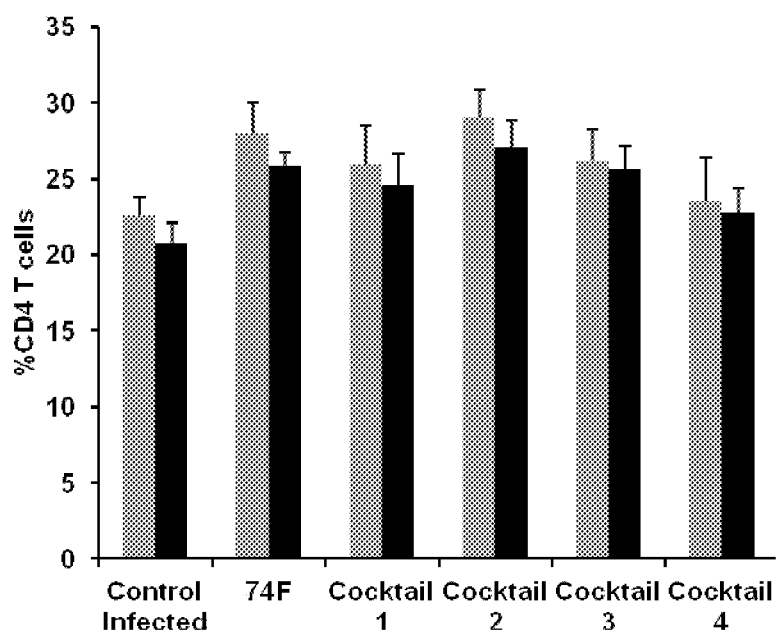
FIG. 11 shows the percentage of CD4+ (A), CD4CD25+ (B), CD8+ (C), and CD8CD25+ (D) T cells in Example 2 from splenocytes stimulated with medium alone (NS) or with a whole cell sonicate of *Mycobacterium avium* subsp. *paratuberculosis* (MPS). Splenocytes were isolated after 3 months of infection from control mice and mice vaccinated with 74F polyprotein or MAP protein cocktails 1-4. Data are expressed as means±SEM. Significant differences between NS and MPS stimulants within a treatment group are represented by asterisks (**P<0.01; *P<0.05).
Figure 11B:
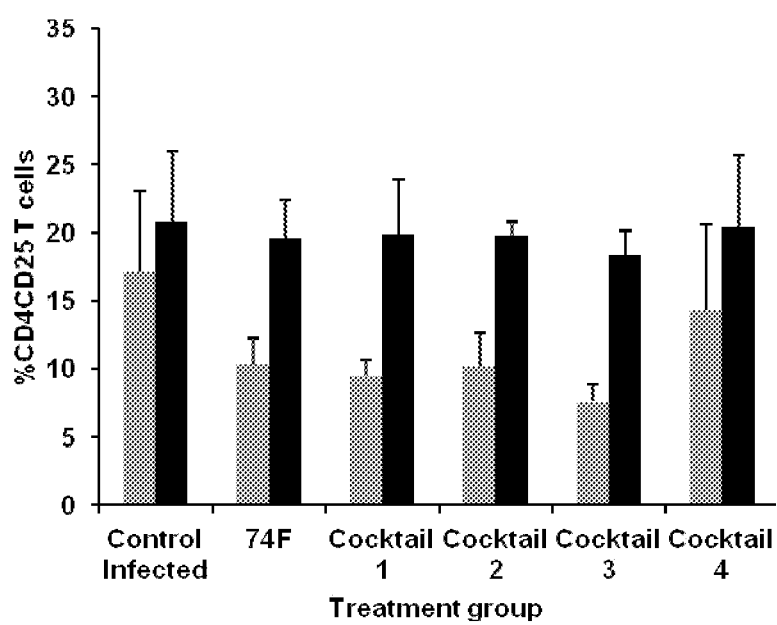
Figure 11C:
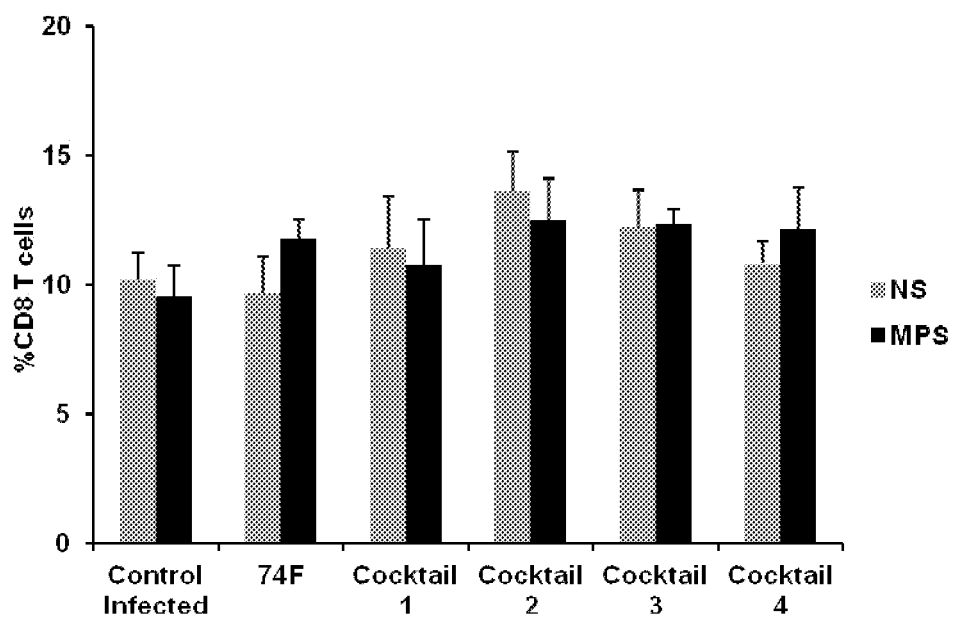
Figure 11D:
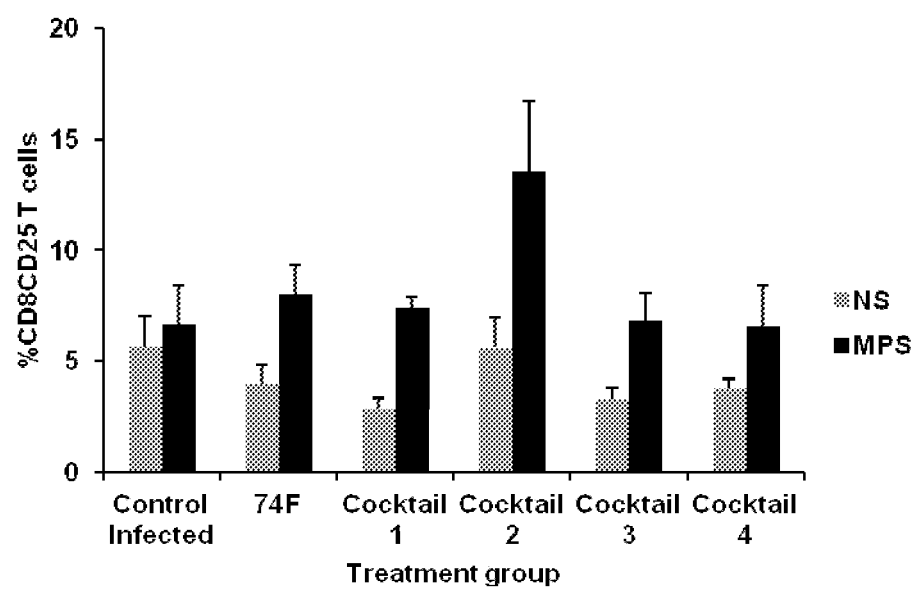

Vaccination with protein cocktails 1-3 and 74F resulted in higher (P<0.05) CD4 T cells compared to control infected mice, regardless of in vitro treatment (FIG. 11A). In addition, immunization of mice with MAP protein cocktails (1-3) or 74F resulted in dramatic (P<0.05) upregulation of CD4CD25 T cells in MPS-stimulated cultures compared to NS cultures (FIG. 11B). There were no major differences in CD8 T cells due to vaccination of mice (FIG. 3C), however, the number of CD8CD25 T cells was significantly (P<0.05) upregulated in MPS-stimulated splenocytes across treatment groups (FIG. 3D). There were no differences in the percentage of γδ T cells and γδCD25+ cells due to vaccination, yet there was a consistent trend towards reduced numbers of these cell types after MPS stimulation of splenocytes in all treatment groups (data not shown). There was a trend for increased total CD25 T cells in mice vaccinated with MAP proteins or 74F although only mice in cocktail 4 had significantly (P<0.05) higher CD25 T cells after MPS stimulation of splenocytes than control infected mice (8.30±1.76 vs 5.46±0.70, respectively; data not shown). Total percentages of CD44, CD62L, and monocytes in splenocyte cultures were unaffected by immunization of mice or in vitro treatment in the present study (data not shown).

B Cells and MAP-Specific Serum $IgG_1$ and $IgG_{2a}$ Results

Figure 12:
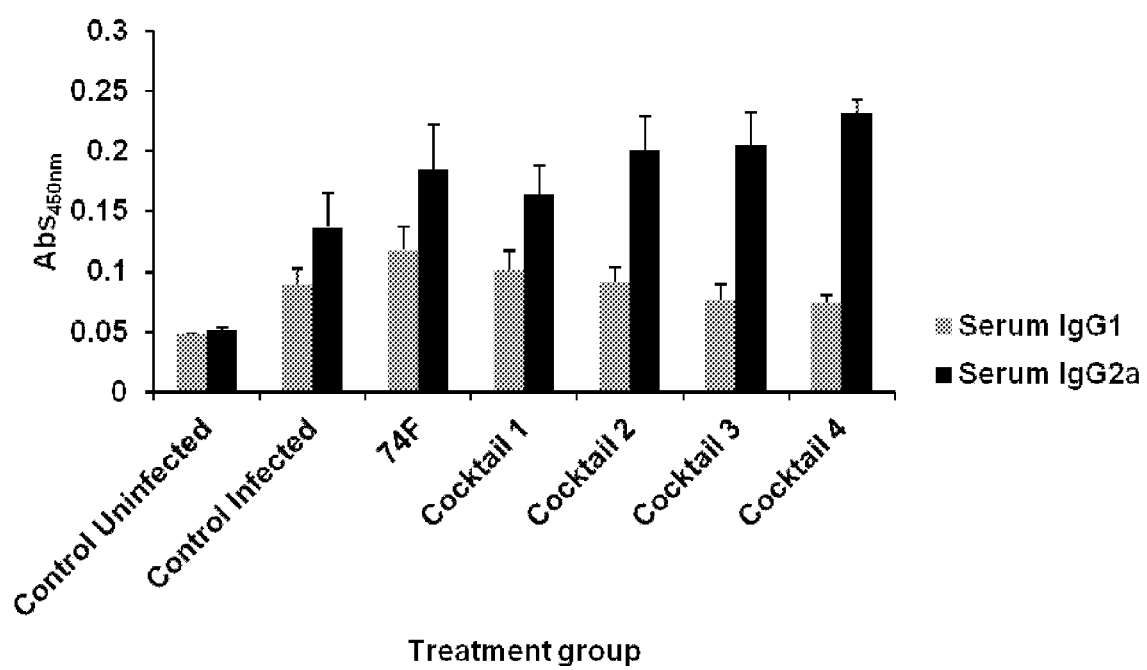
FIG. 12 shows the serum $IgG_1$ and $IgG_{2a}$ antibody responses in Example 2 against *Mycobacterium avium* subsp. *paratuberculosis* after 3 months of infection from control mice and mice vaccinated with 74F polyprotein or MAP protein cocktails 1-4. Data are expressed as means±SEM. Significant differences between control uninfected, control infected and vaccinate groups are represented by asterisks (**P<0.01; *P<0.05).

Interestingly, the percentages of B cells within MPS-stimulated splenocytes were lower (P<0.05) in mice immunized with cocktails 1, 2, and 4, compared to control infected mice (data not shown). Infection with MAP with or without immunization resulted in significant (P<0.05) increases in serum $IgG_1$ and $IgG_{2a}$ compared to control noninfected mice (FIG. 12). Mice immunized with either 74F or the MAP protein cocktails demonstrated increased (P<0.05) MAP-specific serum $IgG_{2a}$ following challenge compared to control infected mice. In contrast, differences due to vaccination were not noted for MAP-specific serum $IgG_1$ antibodies with similar levels noted for all infected mice regardless of vaccination when compared to control infected mice.

Tissue Culture

Figure 13A:
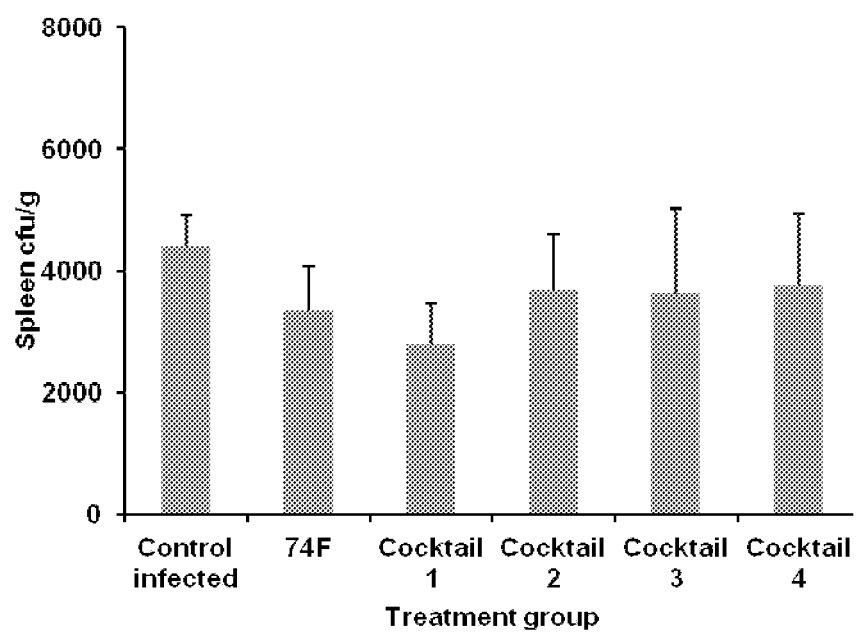
FIG. 13 shows the recovery of viable *Mycobacterium avium* subsp. *paratuberculosis* (cfu/g tissue) in Example 2 from (A) spleen, (B) liver, (C) mesenteric lymph node (MLN), and (D) ileum of control mice and mice vaccinated with 74F polyprotein or MAP protein cocktails 1-4 after 3 months of infection. Data are expressed as means±SEM. Significant differences between control infected and vaccinate groups are represented by asterisks (**P<0.01; *P<0.05).
Figure 13B:
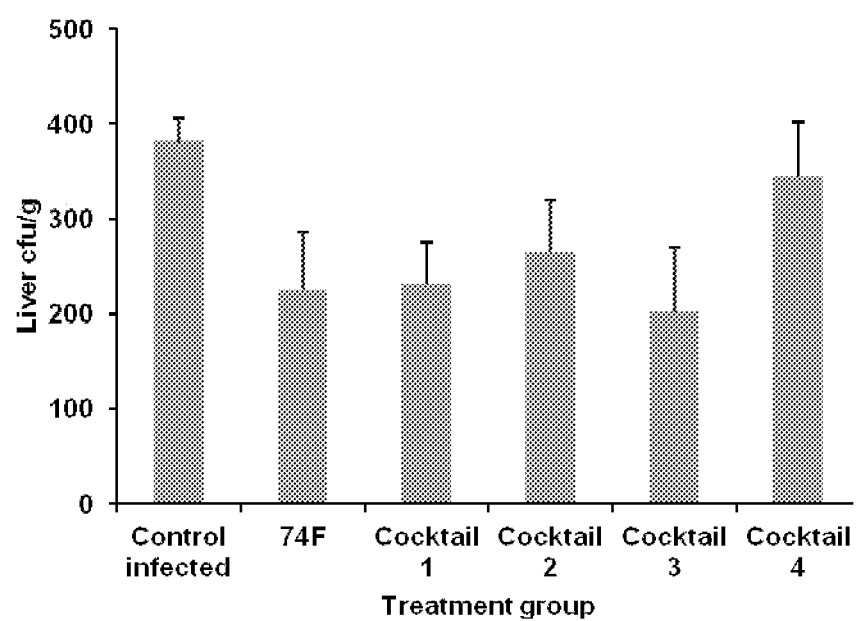
Figure 13C:
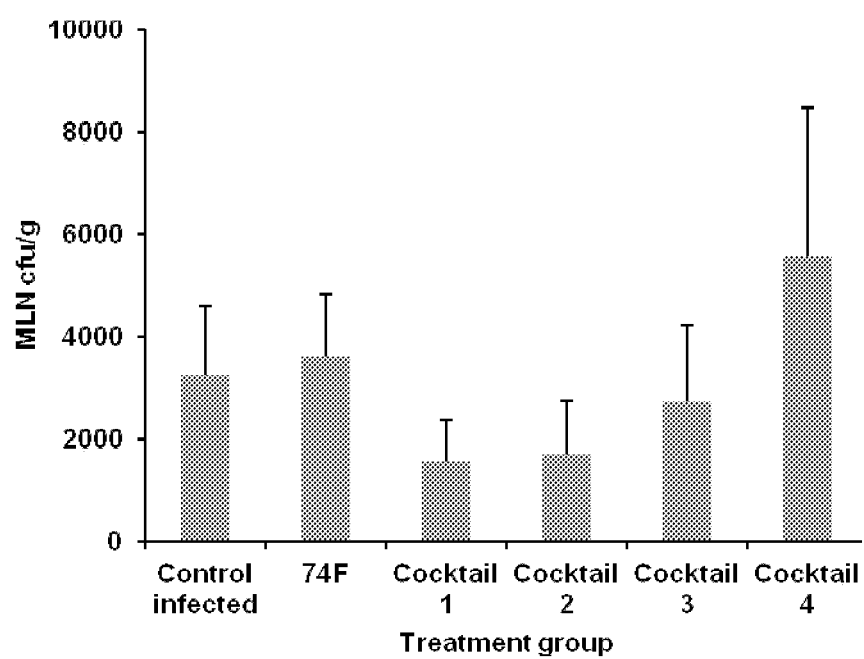
Figure 13D:
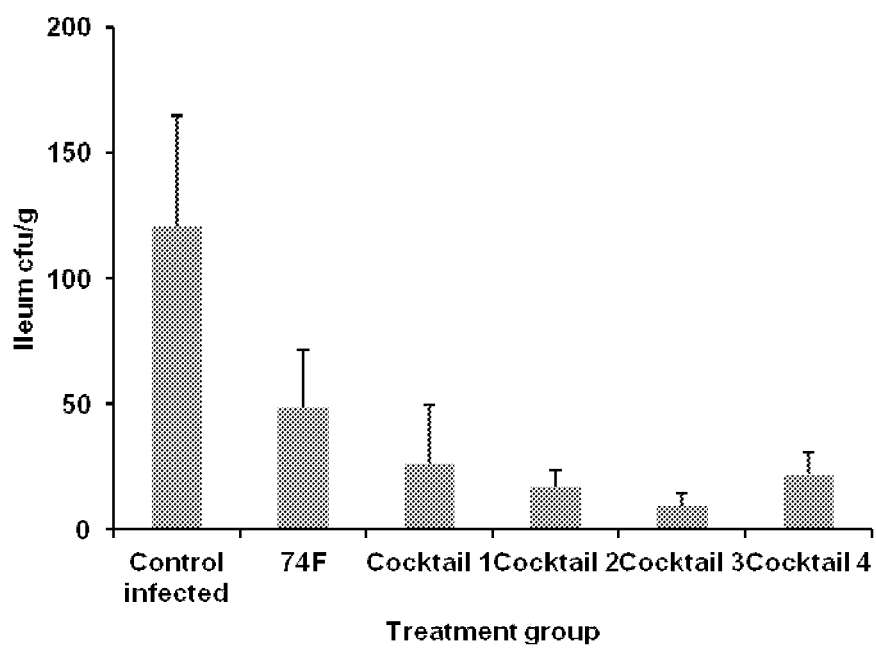

Immunization with cocktails 1-4 did not significantly impact tissue colonization in the spleen after challenge with live MAP, yet there was a trend towards reduced MAP colonization noted in the cocktail 1 group compared to the control infected group (FIG. 13A). Similar reductions in MAP colonization were also noted in the MLN of mice receiving cocktails 1 and 2 prior to challenge, although these differences did not achieve statistical significance (FIG. 13C). However, liver colonization was reduced (P<0.05) in mice immunized with cocktails 1 and 3, as well as the 74F polyprotein that served as a positive control in the study (FIG. 13B). Further, all protein cocktails significantly (P<0.05) reduced MAP colonization in the ileum compared to infected controls (FIG. 13D). Although immunization with the combination of proteins in cocktail 4 (MAP1204, MAP1272c, and MAP2077c) provided less protection against MAP colonization compared to the 3 other cocktails, it was still effective in reducing tissue burden in the ileum.

Discussion

The functions of the four MAP proteins include a peptide transport system permease protein, MAP1087; putative invasion proteins, MAP1204 and MAP1272c; and a STAS domain containing protein, MAP 2077c. Two of the 4 selected proteins (MAP1087 and MAP1204) had previously demonstrated strong reactivity with sera from naturally infected cattle in the subclinical stage of infection (Bannantine et al. Early antibody response against *Mycobacterium avium* subspecies *paratuberculosis* antigens in subclinical cattle. Proteome Sci. 2008. 6:5-16). In addition, MAP1087, MAP1204, and MAP2077c all reacted with sera from experimentally infected calves in the early stage of infection (Bannantine et al. ibid). The selection of these proteins was not based upon specificity to MAP and protein sequence analysis demonstrated significant alignment of all 4 proteins to both MAP and *M. avium*. This is not surprising given the high level of genetic homology (>98%) between MAP and *M. avium*, with few unique genes identified for MAP and even fewer immunogens (Bannantine and Paustian, ibid; Bannantine et al. Development and use of a partial *Mycobacterium avium* subspecies *paratuberculosis* protein array. Proteomics. 2008. 8:463-474). Although partial sequences of MAP1204 were also found in other mycobacterial species, including *M. bovis*, this would not be a major detractor from potential use as a vaccine candidate. Sero-diagnostic tests for the detection of *M. bovis* infection using antigens such as ESAT-6, CFP-10, and MPB83, have demonstrated a lack of cross-reactivity in calves vaccinated with the whole-cell vaccine for MAP (Stabel et al. 2011. ibid). In addition, IFN-g responses to ESAT-6:CFP-10 antigens were observed to be highly specific for calves infected with *M. bovis*, with negligible reactivity noted for MAP- and *M. avium*-infected calves (Waters et al. Use of recombinant ESAT-6:CFP-10 fusion protein for differentiation of infections of cattle by *Mycobacterium bovis* and by *M. avium* subsp. *avium* and *M. avium* subsp. *paratuberculosis*. Clin Diagn Lab Immunol. 2004. 11:729-735) or for calves vaccinated with a whole cell vaccine (Stabel et al. 2011. ibid). This would suggest that adequate tools are available to distinguish between MAP vaccinates and animals infected with *M. bovis*.

Although it is unknown how well immunogenic proteins translate into successful vaccines, it is understood that proteins can be highly antigenic, eliciting both humoral and cell-mediated immune responses. Many researchers utilize immune reactivity in the host as their primary method to screen protein candidates for subunit vaccines, with the hypothesis that an induced response is suggestive of protective immunity. Although proteomic and genomic screening approaches can be used to identify vaccine candidates, these tools are only useful if the candidates are recognized by the host immune system. Screening tools such as Western blotting have been effective for many bacterial pathogens, however, for intracellular pathogens such as MAP, antigen screening should include some measure of responsiveness in a cell-mediated assay since protection is aligned with Th1-mediated immunity in the host (Stabel. Immunology of *paratuberculosis* infection and disease. In: Behr M A. Collins D M, editors. *Paratuberculosis*: Organism, Disease, Control. Cambridge, Mass. CAB International. 2010. p. 230-243). The proteins in the present study were selected upon observation of robust IFN-g responses in naturally infected cattle, combined with the ability to discriminate between infected and noninfected cattle with some measure of specificity.

Numerous infection models have been developed for MAP, with emphasis on ruminant species such as cattle, sheep, goats, deer, and bison (Hines et al. Experimental challenge models for Johne's disease: a review and proposed international guidelines. Vet Microbiol. 2007. 122:197-222) since these are the target species for *paratuberculosis*. However, the protracted period of subclinical infection that occurs in naturally infected hosts is mimicked in experimentally infected animals, resulting in lengthy study periods (Hines et al. ibid; Begg and Whittington. Experimental animal infection models for Johne's disease, an infectious enteropathy caused by *Mycobacterium avium* subsp. *paratuberculosis*. Vet J. 2008. 176:129-145). Mouse models provide a reasonable approach to efficiently evaluate vaccine candidates due to a shorter infection periods compared to ruminants, greater reproducibility due to more precise genetics amongst treatment animals, and reduced costs for care and housing, allowing for greater numbers of animals per treatment group. Mouse models for MAP infection have been adequately characterized and IP infection of Balb/c mice results in effective colonization of the major target tissues (Talaat. Experimental small animal models of *paratuberculosis*. In: Behr M A, Collins D M, editors. *Paratuberculosis*: Organism, Disease, Control. Cambridge, Mass. CAB International. 2010. p. 223-227).

Th1-mediated immune responses may be indicative of exposure to mycobacterial pathogens, including MAP, but also appear to be essential to keep infection from progressing from subclinical to clinical disease. In a neonatal calf infection model, we were able to demonstrate the upregulation of immune markers including, robust antigen-specific IFN-γ responses as well as induction of antigen-specific CD25, CD26, and CD45RO expression less than 3 months after infection (Stabel and Robbe-Austerman. Early immune markers associated with *Mycobacterium avium* subsp. *paratuberculosis* infection in a neonatal calf model. Clin Vaccine Immunol. 2011. 18:393-405). Although Th2 responses are not known to be protective in the host, both Th1- and Th2-mediated immunity has been induced after vaccination with a whole cell preparation of MAP (Gillan et al. Ovine immune parameters following immunization against *Mycobacterium avium* ssp. *paratuberculosis* using a lipid-based live-cell vaccine. Vet Immunol Immunopathol. 2010. 109-119; Platt et al. Evaluation of the cell-mediated immune response to reduced doses of *Mycobacterium avium* ssp. *paratuberculosis* vaccine in cattle. Vet Immunol Immunopathol. 2010. 122-126; and Kathaperumal et al. Evaluation of immune responses and protective efficacy in a goat model following immunization with a cocktail of recombinant antigens and a polyprotein of *Mycobacterium avium* subsp. *paratuberculosis*. Vaccine. 2009. 27:123-35). Recent studies have also demonstrated that MAP vaccines comprised of single proteins or protein complexes will also evoke strong Th1 responses (Koets et al. ibid; Chen et al. ibid; Kathaperumal et al. 2008. ibid; Kathaperumal et al. 2009. ibid; and Nguyen et al. Immune response of cattle immunized with a conjugate of the glycolipid glucose monomycolate and protein. Vet Immunol Immunopathol. 2011. 142:265-70). In the present study, immunization of mice with MAP protein cocktails prior to challenge with live MAP resulted in similar induction of antigen-specific IFN-γ when compared to control infected mice, although some attenuation of the IFN-γ response was noted. Differences in IFN-γ secretion between NS and MPS-stimulated cultures were lower for mice vaccinated with protein cocktails, particularly cocktail 1. This would suggest that immunization with this triad of proteins may have resulted in greater constitutive secretion of IFN-γ but lower antigen-specific IFN-γ secretion after challenge, an effect that may be advantageous to the host. Pro-inflammatory effects of IFN-γ can be both beneficial and detrimental to the host and a finite balance must be achieved in order to maintain effective immunity (Schroder et al. Interferon-gamma: an overview of signals, mechanisms, and functions. J Leuko Biol. 2004. 75:163-9). Interleukin-23 was upregulated by MAP infection, with increased secretion noted after stimulation with MPS antigen in vitro for all treatment groups. This is the first study describing effects of MAP infection on the secretion of IL-23. IL-23 is a newly recognized cytokine that is involved in the inflammatory response to mycobacterial infections, although little is known about its role in the immunopathology of MAP infections. IL-23 is required for the generation of effector memory T cells and is also needed for generation of IL-17-producing T cells, which play an important role in the inflammatory response (Khader and Cooper. IL-23 and IL-17 in tuberculosis. Cytokine. 41:79-83).

Although Th2-mediated cytokine production was not markedly different due to vaccination, an interesting observation was the pattern of IL-4 secretion noted between NS and MPS-stimulated splenocytes in mice vaccinated with MAP protein cocktails, particularly for mice immunized with cocktail 1. Vaccination with MAP proteins 1087, 1204, and 1272c, in cocktail 1 resulted in higher constitutive secretion of IL-4 compared to the other treatment groups, something that was not apparent upon further exposure of splenocytes to MAP antigen in vitro. These results would suggest that this cocktail of MAP proteins modulated Th2 responses of the host after infection, an important consideration for selection of vaccine candidates. This is further substantiated by the increase in MAP-specific serum $IgG_{2a}$ noted for mice immunized with either 74F or MAP protein cocktails. Secretion of $IgG_{2a}$ antibodies is most closely associated with Th1-mediated immunity and cytokines such as IFN-γ, IL-4, and IL-10 can influence the isotype switch to $IgG_{2a}$ (Stevens et al. Regulation of antibody isotype secretion by subsets of antigen-specific helper T cells. Nature. 1998. 334:255-258).

Immune responses to vaccination are critical for the control of infection in the host. Immunization with the MAP protein cocktails effectively reduced MAP colonization of the liver and ileum. In particular, cocktail 1 also demonstrated efficacy for reduced colonization of the spleen and mesenteric lymph node, providing the most consistent effect on retardation of infection in the host. Reduced colonization of tissues is a beneficial characteristic for *paratuberculosis* vaccines and has been reported for commercial vaccines such as Mycopar and Gudair, as well as for more recently developed subunit vaccines (Koets et al. ibid; Kathaperumal et al. 2008. ibid; Patton. Vet Clin North Am Food Anim Pract. 2011. 27:573-580; Reddacliff et al. Efficacy of a killed vaccine for the control of *paratuberculosis* in Australian sheep flocks. Vet Micro. 2006. 115:77-90). Decreased tissue burdens result in reduced shedding of MAP in the feces thereby allaying spread of infection within a herd (Kalis et al. Use of long-term vaccination with a killed vaccine to prevent fecal shedding of *Mycobacterium avium* subsp. *paratuberculosis* in dairy herds. Am J Vet Res. 2001. 62:270-274). Similar reductions in tissue burden have been reported for mice immunized with the 74F polyprotein, with reduced recoveries of viable MAP from spleen, liver and mesenteric lymph nodes at 12 and 16 weeks post-challenge (Chen et al. ibid). The highly positive results achieved with the 74F polyprotein prompted us to incorporate it into our study as a positive control. The Mycopar vaccine was an undesirable choice as a positive control vaccine in the current study as effects have not been previously evaluated in a mouse model. In addition, the Mycopar vaccine typically causes large granulomatous nodules at the injection site in ruminants, an effect that would not be handled well in a young mouse (Patton. ibid). In ruminants, this local inflammatory effect is managed somewhat by injecting the vaccine in the fatty area of the brisket. Much of the benefit previously noted for this immunogen was repeated in the present study, with concurrent reductions in tissue colonization and activation of T cells as previously described. Despite this, cocktail 1 seemed to invoke the most consistent responses in protection against tissue colonization. Further, this triad of MAP proteins, 1087, 1204, and 1272c, appeared to more tightly regulate the immune response post-immunization both before and after challenge with live MAP. Host responses after immunization with either cocktail 2 or 3 more closely aligned themselves to results observed for cocktail 1. The common protein between these 3 cocktails was MAP1087, whose known function is a peptide transport system permease protein.

In summary, the present study evaluated cocktails of MAP proteins as potential subunit vaccines for *paratuberculosis*. Cocktails of MAP proteins proved effective in protection against tissue colonization and invoked cell-mediated and humoral immunity in the host.

It is understood that the foregoing detailed description is given merely by way of illustration and that modifications and variations may be made therein without departing from the spirit and scope of the invention.

We claim:

1. A composition comprising isolated and purified immunogenic proteins of *Mycobacterium avium* subspecies *paratuberculosis* and a pharmaceutically acceptable carrier, wherein said immunogenic proteins are provided in an amount effective to stimulate an immune response in an animal against said *Mycobacterium avium* subspecies *paratuberculosis*, and said immunogenic proteins comprise MAP1087 and at least two of MAP1204, MAP1272c, and MAP2077c wherein said MAP1087 comprises SEQ ID NO: 1; wherein said MAP1204 comprises SEQ ID NO: 2; wherein said MAP1272c comprises SEQ ID NO: 3; and wherein said MAP2077c comprises SEQ ID NO: 4, wherein said pharmaceutically acceptable carrier is selected from the group consisting of physiological saline, phosphate buffered saline, mineral oil, vegetable oil, aqueous carboxymethyl cellulose, and polyvinylpyrrolidone.

2. The composition of claim 1 further comprising an adjuvant.

3. The composition of claim 1 wherein said immunogenic proteins comprise MAP1087, MAP1204 and MAP1272c.

4. The composition of claim 1 wherein said immunogenic proteins comprise MAP1087, MAP1204 and MAP2077c.

5. The composition of claim 1 wherein said immunogenic proteins comprise MAP1087, MAP1272c and MAP2077c.

6. The composition of claim 1 wherein said immunogenic proteins comprise MAP1087, MAP1204, MAP1272c and MAP2077c.

7. An immunogenic composition comprising fusion protein MAP1087/MBP and at least two of the fusion proteins MAP1204/MBP, MAP1272c/MBP, and MAP2077c/MBP wherein said MAP1087/MBP comprises SEQ ID NO: 5, said MAP1204/MBP comprises SEQ ID NO: 6, said MAP1272c/MBP comprises SEQ ID NO: 7 and said MAP2077c/MBP comprises SEQ ID NO: 8.

8. A method for reducing *Mycobacterium avium* subspecies *paratuberculosis* colonization in an animal comprising administering to said animal an immunologically effective dose of a composition comprising a pharmaceutically acceptable carrier, isolated and purified MAP1087 and at least two of isolated and purified MAP1204, isolated and purified MAP1272c, and isolated and purified MAP2077c; wherein said MAP1087 comprises SEQ ID NO: 1, MAP1204 comprises SEQ ID NO: 2, MAP1272c comprises SEQ ID NO: 3, and MAP2077c comprises SEQ ID NO: 4, wherein said immunologically effective dose causes said animal to generate an immune response sufficient to protect said animal from infection with said *Mycobacterium avium* subspecies *paratuberculosis*; and wherein said pharmaceutically acceptable carrier is selected from the group consisting of physiological saline, phosphate buffered saline, mineral oil, vegetable oil, aqueous carboxymethyl cellulose, and polyvinylpyrrolidone.

9. The method of claim 8 wherein said animal is a ruminant.

10. The method of claim 9 wherein said animal is selected from the group consisting of bovine, ovine and caprine.

11. The method of claim 8 wherein said composition further comprises an adjuvant.

12. The method of claim 8 wherein said composition comprises MAP1087, MAP1204 and MAP1272c.

13. The method of claim 8 wherein said composition comprises MAP1087, MAP1204 and MAP2077c.

14. The method of claim 8 wherein said composition comprises MAP1087 and MAP1272c and MAP2077c.

15. The method of claim 8 wherein said composition comprises MAP1087, MAP1204, MAP1272c and MAP2077c.

16. A method for reducing *Mycobacterium avium* subspecies *paratuberculosis* colonization in an animal comprising administering to said animal an immunologically effective dose of a immunogenic composition comprising fusion protein MAP1087/MBP and at least two of the fusion proteins MAP1204/MBP, MAP1272c/MBP, and MAP2077c/MBP, wherein said MAP1087/MBP comprises SEQ ID NO: 5, said MAP1204/MBP comprises SEQ ID NO: 6, said MAP1272c/MBP comprises SEQ ID NO: 7 and said MAP2077c/MBP comprises SEQ ID NO: 8, wherein said immunologically effective dose causes said animal to generate an immune response sufficient to protect said animal from infection with said *Mycobacterium avium* subspecies *paratuberculosis*.

17. The method of claim 16 wherein said animal is a ruminant.

18. The method of claim 16 wherein said composition further comprises an adjuvant.

19. A method of generating a Th1 immune response against *Mycobacterium avium* subspecies *paratuberculosis* in an animal comprising administering to said animal a composition in an amount sufficient to generate a Th1 immune response in said animal, said composition comprising a pharmaceutically acceptable carrier, isolated and purified MAP1087 and at least two of isolated and purified MAP1204, isolated and purified MAP1272c, and isolated and purified MAP2077c; wherein said MAP1087 comprises SEQ ID NO: 1, MAP1204 comprises SEQ ID NO: 2, MAP1272c comprises SEQ ID NO: 3, and MAP2077c comprises SEQ ID NO: 4; and wherein said pharmaceutically acceptable carrier is selected from the group consisting of physiological saline, phosphate buffered saline, mineral oil, vegetable oil, aqueous carboxymethyl cellulose, and polyvinylpyrrolidone.

20. The method of claim 19 wherein said animal is a ruminant.

21. The method of claim 19 wherein said composition further comprises an adjuvant.

22. The method of claim 19 wherein said composition comprises MAP1087, MAP1204, and MAP1272c.

23. The method of claim 19 wherein said composition comprises MAP1087, MAP1204, and MAP2077c.

24. The method of claim 19 wherein said composition comprises MAP1087, MAP1272c, and MAP2077c.

25. The method of claim 19 wherein said composition comprises MAP1087, MAP1204, MAP1272c, and MAP2077c.

26. A method of generating a Th1 immune response against *Mycobacterium avium* subspecies *paratuberculosis* in an animal comprising administering to said animal an composition in an amount sufficient to generate a Th1 immune response in said animal, said composition comprising fusion protein MAP1087/MBP and at least two of the fusion proteins MAP1204/MBP, MAP1272c/MBP, and MAP2077c/MBP, wherein said MAP1087/MBP comprises SEQ ID NO: 5, said MAP1204/MBP comprises SEQ ID NO: 6, said MAP1272c/MBP comprises SEQ ID NO: 7 and said MAP2077c/MBP comprises SEQ ID NO: 8.

27. The method of claim 26 wherein said animal is a ruminant.

28. The method of claim 26 wherein said composition further comprises an adjuvant.

29. The method of claim 28 wherein said amount contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

30. The method of claim 26 wherein said amount contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

31. The method of claim 19 wherein said amount contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

32. The method of claim 21 wherein said amount contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

33. The method of claim 16 wherein said immunologically effective dose contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

34. The method of claim 18 wherein said immunologically effective dose contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

35. The method of claim 8 wherein said immunologically effective dose contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

36. The method of claim 11 wherein said immunologically effective dose contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

37. The immunogenic composition of claim 7 further comprising an adjuvant.

38. The immunogenic composition of claim 37 wherein said immunogenic composition contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

39. The immunogenic composition of claim 7 wherein said fusion proteins comprise MAP1087/MBP, MAP1204/MBP, and MAP1272c/MBP.

40. The immunogenic composition of claim 7 wherein said fusion proteins comprise MAP1087/MBP, MAP1204/MBP, and MAP2077c/MBP.

41. The immunogenic composition of claim 7 wherein said fusion proteins comprise MAP1087/MBP, MAP1272c/MBP, and MAP2077c/MBP.

42. The immunogenic composition of claim 7 wherein said fusion proteins comprise MAP1087/MBP, MAP1204/MBP, MAP1272c/MBP, and MAP2077c/MBP.

43. The immunogenic composition of claim 7 wherein said immunogenic composition contains approximately 0.1 mg to approximately 0.5 mg of said MAP1087/MBP, and approximately 0.1 mg to approximately 0.5 mg of each of said at least two of MAP1204/MBP, MAP1272c/MBP, and MAP2077c/MBP.

44. The immunogenic composition of claim 1 wherein said immunogenic composition contains approximately 0.1 mg to approximately 0.5 mg of said MAP1087, and approximately 0.1 mg to approximately 0.5 mg of each of said at least two of MAP1204, MAP1272c, and MAP2077c.

45. The immunogenic composition of claim 2 wherein said immunogenic composition contains approximately 0.1 mg to approximately 0.5 mg of said MAP1087, and approximately 0.1 mg to approximately 0.5 mg of each of said at least two of MAP1204, MAP1272c, and MAP2077c.

* * * * *

SEQUENCE LISTING

```
<160> NUMBER OF SEQ ID NOS: 12

<210> SEQ ID NO 1
<211> LENGTH: 146
<212> TYPE: PRT
<213> ORGANISM: Mycobacterium avium

<400> SEQUENCE: 1

Met Leu Gly Tyr Val Leu Ala Arg Ile Gly Gln Ser Ala Ile Val Leu
1               5                   10                  15

Leu Ala Val Phe Ser Leu Val Phe Trp Gly Val Ser Ile Leu Pro Ala
                20                  25                  30

Asp Pro Ala Ala Ile Phe Val Ala Lys Gly Glu Gly Tyr Phe Asn Pro
            35                  40                  45

Asp Ile Val Ala Gln Val Lys Ala Phe Tyr Gly Tyr Asp Arg Pro Leu
        50                  55                  60

Trp Val Gln Tyr Phe Ala Gln Leu Asn Gln Val Leu His Gly His Phe
65                  70                  75                  80

Gly Phe Ser Leu Ser Ser Gly Gln Ala Val Thr Asp Arg Ile Gly Gly
                85                  90                  95

Val Ile Gly Glu Thr Leu Lys Leu Ala Ala Thr Ala Thr Gly Phe Ala
            100                 105                 110

Val Leu Phe Ala Val Ser Val Thr Ala Leu Ala Thr Thr Cys Ala Pro
        115                 120                 125

Val Arg Ser Val Leu Arg Ala Ile Pro Pro Leu Phe Gly Ala Val Pro
    130                 135                 140

Thr Phe
145

<210> SEQ ID NO 2
<211> LENGTH: 244
<212> TYPE: PRT
<213> ORGANISM: Mycobacterium avium

<400> SEQUENCE: 2

Met Arg Arg Asn Arg Phe Arg Leu Ile Val Phe Ala Trp Ile Thr Ala
1               5                   10                  15

Met Val Thr Gly Leu Met Phe Ser Val Ala Pro Thr Pro Ala Ala Leu
                20                  25                  30

Ala Asp Pro Gly Glu Trp Asp Pro Thr Leu Pro Ala Gln Ile Ser Ala
            35                  40                  45

Gly Ala Pro Gly Asp Pro Leu Ala Val Ala Asn Ala Ser Leu Gln Ala
        50                  55                  60

Thr Ala Gln Ala Thr Gln Thr Thr Leu Asn Leu Gly Lys Gln Phe Leu
65                  70                  75                  80

Gly Gly Leu Gly Ile Asn Leu Gly Gly Asn Asp Ala Pro Ala Ala Ala
                85                  90                  95

Ala Thr Pro Ser Asn Pro Gly Gly Lys Ile Pro Arg Val Tyr Gly Arg
            100                 105                 110
```

```
Gln Ala Ile Glu Tyr Val Ile Lys Arg Met Gly Ser Gln Met Gly Val
        115                 120                 125

Pro Tyr Ser Trp Gly Gly Ser Leu Asp Gly Pro Ser Lys Gly Val
130                 135                 140

Gly Asp Gly Ala Asn Ile Thr Gly Phe Asp Cys Ser Gly Leu Met Arg
145                 150                 155                 160

Tyr Gly Phe Ala Gly Val Gly Val Leu Ile Pro Arg Phe Ser Gly Asp
                165                 170                 175

Gln Tyr Asn Ala Gly Arg His Ile Pro Gln Asp Gln Ala Arg Arg Gly
            180                 185                 190

Asp Leu Ile Phe Tyr Gly Pro Gly Gly Ser Gln His Val Thr Met Tyr
        195                 200                 205

Leu Gly Asn Gly Gln Met Leu Glu Ala Ser Ser Ala Gly Lys Val
    210                 215                 220

Thr Val Ser Pro Val Arg Lys Pro Gly Met Thr Pro Phe Leu Thr Arg
225                 230                 235                 240

Ile Ile Glu Tyr

<210> SEQ ID NO 3
<211> LENGTH: 316
<212> TYPE: PRT
<213> ORGANISM: Mycobacterium avium

<400> SEQUENCE: 3

Val Arg Ser Gln Arg Gly Gly Pro Arg Val His Glu Pro Gly Arg
1               5                   10                  15

Thr Arg Glu Val Thr Ala Pro Arg Pro Asp Glu Cys Arg Arg Gly Gln
                20                  25                  30

Glu Arg Pro Gly Lys Met Lys Arg Ile Tyr Ala Phe Ala Ile Gly Leu
            35                  40                  45

Ala Leu Leu Gly Ala Pro Ala Ala Pro Met Val Val Pro Pro Val Ala
50                  55                  60

Thr Ala Asp Pro Gly Val Arg Ala Met Asp Tyr Gln Gln Ala Thr Asp
65                  70                  75                  80

Val Val Ile Ala Arg Gly Leu Ser Gln Arg Gly Val Pro Phe Ser Trp
                85                  90                  95

Ala Gly Gly Gly Ile Asn Gly Pro Thr Arg Gly Thr Gly Thr Gly Ala
            100                 105                 110

Asn Thr Val Gly Phe Asp Ala Ser Gly Leu Met Gln Tyr Ala Tyr Ala
        115                 120                 125

Gly Ala Gly Ile Lys Leu Pro Arg Ser Ser Gly Ala Met Tyr Arg Val
    130                 135                 140

Gly Gln Lys Ile Leu Pro Gln Gln Ala Arg Lys Gly Asp Leu Ile Phe
145                 150                 155                 160

Tyr Gly Pro Glu Gly Thr Gln Ser Val Ala Met Tyr Leu Gly Asn Asn
                165                 170                 175

Gln Met Leu Glu Val Gly Asp Val Val Gln Val Ser Pro Val Arg Thr
            180                 185                 190

Ala Gly Met Ala Pro Tyr Met Val Arg Val Leu Gly Thr Thr Ala Pro
        195                 200                 205

Thr Gln Gln Val Pro Gln Gln Ala Pro Leu Gln Gln Thr Pro Ala Gln
    210                 215                 220

Gln Ala Pro Leu Gln Gln Thr Pro Gly Gln Gln Ala Pro Leu Gln Gln
225                 230                 235                 240
```

```
Thr Pro Gly Gln Gln Leu Pro Thr Gln Ala Pro Leu Gln Val
                245                 250                 255

Pro Gly Gln Gln Val Pro Gly Gln Gln Leu Pro Thr Gln Ala Pro
            260                 265                 270

Gln Gln Ala Pro Leu Gln Leu Ala Pro Thr Gln Ala Pro Leu Gln
            275                 280                 285

Gln Leu Pro Thr Gln Ser Pro Leu Gln Gln Leu Pro Val Gln Gln
            290                 295                 300

Ser Pro Leu Gln Pro Ala Gly Ala Gly Leu Thr Arg
305                 310                 315

<210> SEQ ID NO 4
<211> LENGTH: 109
<212> TYPE: PRT
<213> ORGANISM: Mycobacterium avium

<400> SEQUENCE: 4

Met Val Thr Pro Leu Thr Leu Asp Thr Gly Arg Gly Ser Asp Gly Asn
1               5                   10                  15

Pro Val Leu Val Ala Val Gly Glu Ile Asp Leu Ser Asn Ile Asp Ala
            20                  25                  30

Phe His Arg Ala Leu Ala Thr Ala Thr Ala Glu Val Thr Gly Ser Asp
        35                  40                  45

Gly Ala Val Leu Val Asp Leu Ser Ala Val Glu Tyr Val Asp Ser Ala
    50                  55                  60

Ala Ile Asn Ala Leu Ala Ala His Ala Asp His Ile Ala Leu Val Ala
65                  70                  75                  80

His Pro Val Leu Met Pro Val Phe Arg Val Ser Gly Leu Thr Glu Leu
                85                  90                  95

Thr Thr Val Glu Ala Ala Pro Pro Pro Ala Pro Arg
            100                 105

<210> SEQ ID NO 5
<211> LENGTH: 541
<212> TYPE: PRT
<213> ORGANISM: Mycobacterium avium

<400> SEQUENCE: 5

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140
```

```
Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
            370                 375                 380

Glu Gly Arg Ile Ser Glu Phe Gly Ser Ser Arg Met Leu Gly Tyr Val
385                 390                 395                 400

Leu Ala Arg Ile Gly Gln Ser Ala Ile Val Leu Leu Ala Val Phe Ser
                405                 410                 415

Leu Val Phe Trp Gly Val Ser Ile Leu Pro Ala Asp Pro Ala Ala Ile
            420                 425                 430

Phe Val Ala Lys Gly Glu Gly Tyr Phe Asn Pro Asp Ile Val Ala Gln
            435                 440                 445

Val Lys Ala Phe Tyr Gly Tyr Asp Arg Pro Leu Trp Val Gln Tyr Phe
450                 455                 460

Ala Gln Leu Asn Gln Val Leu His Gly His Phe Gly Phe Ser Leu Ser
465                 470                 475                 480

Ser Gly Gln Ala Val Thr Asp Arg Ile Gly Gly Val Ile Gly Glu Thr
                485                 490                 495

Leu Lys Leu Ala Ala Thr Ala Thr Gly Phe Ala Val Leu Phe Ala Val
            500                 505                 510

Ser Val Thr Ala Leu Ala Thr Thr Cys Ala Pro Val Arg Ser Val Leu
            515                 520                 525

Arg Ala Ile Pro Pro Leu Phe Gly Ala Val Pro Thr Phe
530                 535                 540

<210> SEQ ID NO 6
<211> LENGTH: 639
```

<212> TYPE: PRT
<213> ORGANISM: Mycobacterium avium

<400> SEQUENCE: 6

```
Met Lys Ile Glu Gl

```
Phe Arg Leu Ile Val Phe Ala Trp Ile Thr Ala Met Val Thr Gly Leu
                405                 410                 415

Met Phe Ser Val Ala Pro Thr Pro Ala Leu Ala Asp Pro Gly Glu
        420                 425                 430

Trp Asp Pro Thr Leu Pro Ala Gln Ile Ser Ala Gly Ala Pro Gly Asp
                435                 440                 445

Pro Leu Ala Val Ala Asn Ala Ser Leu Gln Ala Thr Ala Gln Ala Thr
450                 455                 460

Gln Thr Thr Leu Asn Leu Gly Lys Gln Phe Leu Gly Leu Gly Ile
465                 470                 475                 480

Asn Leu Gly Gly Asn Asp Ala Pro Ala Ala Ala Thr Pro Ser Asn
                485                 490                 495

Pro Gly Gly Lys Ile Pro Arg Val Tyr Gly Arg Gln Ala Ile Glu Tyr
                500                 505                 510

Val Ile Lys Arg Met Gly Ser Gln Met Gly Val Pro Tyr Ser Trp Gly
            515                 520                 525

Gly Gly Ser Leu Asp Gly Pro Ser Lys Gly Val Gly Asp Gly Ala Asn
        530                 535                 540

Ile Thr Gly Phe Asp Cys Ser Gly Leu Met Arg Tyr Gly Phe Ala Gly
545                 550                 555                 560

Val Gly Val Leu Ile Pro Arg Phe Ser Gly Asp Gln Tyr Asn Ala Gly
                565                 570                 575

Arg His Ile Pro Gln Asp Gln Ala Arg Arg Gly Asp Leu Ile Phe Tyr
                580                 585                 590

Gly Pro Gly Gly Ser Gln His Val Thr Met Tyr Leu Gly Asn Gly Gln
            595                 600                 605

Met Leu Glu Ala Ser Gly Ser Ala Gly Lys Val Thr Val Ser Pro Val
        610                 615                 620

Arg Lys Pro Gly Met Thr Pro Phe Leu Thr Arg Ile Ile Glu Tyr
625                 630                 635

<210> SEQ ID NO 7
<211> LENGTH: 711
<212> TYPE: PRT
<213> ORGANISM: Mycobacterium avium

<400> SEQUENCE: 7

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
```

```
                130                 135                 140
Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Ile
                370                 375                 380

Glu Gly Arg Ile Ser Glu Phe Gly Ser Ser Arg Val Arg Ser Gln Arg
385                 390                 395                 400

Gly Gly Pro Arg Pro Val His Glu Pro Gly Arg Thr Arg Glu Val Thr
                405                 410                 415

Ala Pro Arg Pro Asp Glu Cys Arg Arg Gly Gln Glu Arg Pro Gly Lys
                420                 425                 430

Met Lys Arg Ile Tyr Ala Phe Ala Ile Gly Leu Ala Leu Leu Gly Ala
                435                 440                 445

Pro Ala Ala Pro Met Val Val Pro Val Ala Thr Ala Asp Pro Gly
        450                 455                 460

Val Arg Ala Met Asp Tyr Gln Gln Ala Thr Asp Val Ile Ala Arg
465                 470                 475                 480

Gly Leu Ser Gln Arg Gly Val Pro Phe Ser Trp Ala Gly Gly Ile
                485                 490                 495

Asn Gly Pro Thr Arg Gly Thr Gly Thr Gly Ala Asn Thr Val Gly Phe
                500                 505                 510

Asp Ala Ser Gly Leu Met Gln Tyr Ala Tyr Ala Gly Ala Gly Ile Lys
                515                 520                 525

Leu Pro Arg Ser Ser Gly Ala Met Tyr Arg Val Gly Gln Lys Ile Leu
                530                 535                 540

Pro Gln Gln Ala Arg Lys Gly Asp Leu Ile Phe Tyr Gly Pro Glu Gly
545                 550                 555                 560
```

```
Thr Gln Ser Val Ala Met Tyr Leu Gly Asn Asn Gln Met Leu Glu Val
                565                 570                 575

Gly Asp Val Val Gln Val Ser Pro Val Arg Thr Ala Gly Met Ala Pro
            580                 585                 590

Tyr Met Val Arg Val Leu Gly Thr Thr Ala Pro Thr Gln Gln Val Pro
        595                 600                 605

Gln Gln Ala Pro Leu Gln Gln Thr Pro Ala Gln Gln Ala Pro Leu Gln
    610                 615                 620

Gln Thr Pro Gly Gln Gln Ala Pro Leu Gln Gln Thr Pro Gly Gln Gln
625                 630                 635                 640

Leu Pro Thr Gln Gln Ala Pro Leu Gln Gln Val Pro Gly Gln Gln Val
                645                 650                 655

Pro Gly Gln Gln Leu Pro Thr Gln Gln Ala Pro Gln Gln Ala Pro Leu
            660                 665                 670

Gln Leu Ala Pro Thr Gln Gln Ala Pro Leu Gln Gln Leu Pro Thr Gln
        675                 680                 685

Gln Ser Pro Leu Gln Gln Leu Pro Val Gln Gln Ser Pro Leu Gln Pro
    690                 695                 700

Ala Gly Ala Gly Leu Thr Arg
705                 710

<210> SEQ ID NO 8
<211> LENGTH: 504
<212> TYPE: PRT
<213> ORGANISM: Mycobacterium avium

<400> SEQUENCE: 8

Met Lys Ile Glu Glu Gly Lys Leu Val Ile Trp Ile Asn Gly Asp Lys
1               5                   10                  15

Gly T

```
              210                 215                 220
Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser Ser Arg Met Val Thr Pro Leu
385                 390                 395                 400

Thr Leu Asp Thr Gly Arg Gly Ser Asp Gly Asn Pro Val Leu Val Ala
                405                 410                 415

Val Gly Glu Ile Asp Leu Ser Asn Ile Asp Ala Phe His Arg Ala Leu
            420                 425                 430

Ala Thr Ala Thr Ala Glu Val Thr Gly Ser Asp Gly Ala Val Leu Val
        435                 440                 445

Asp Leu Ser Ala Val Glu Tyr Val Asp Ser Ala Ala Ile Asn Ala Leu
    450                 455                 460

Ala Ala His Ala Asp His Ile Ala Leu Val Ala His Pro Val Leu Met
465                 470                 475                 480

Pro Val Phe Arg Val Ser Gly Leu Thr Glu Leu Thr Thr Val Glu Ala
                485                 490                 495

Ala Pro Pro Pro Pro Ala Pro Arg
            500

<210> SEQ ID NO 9
<211> LENGTH: 1626
<212> TYPE: DNA
<213> ORGANISM: Mycobacterium avium

<400> SEQUENCE: 9
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt atcgctgat ttataacaaa      360 gatctgctgc cgaaccccgcc aaaaacctgg gaagagatcc cggcgctgga taagaaactg     420
aaagcgaaag gtaagagcgc gctgatgttc aacctgcaag aaccgtactt cacctggccg     480
```

```
ctgattgctg ctgacggggg ttatgcgttc aagtatgaaa acggcaagta cgacattaaa    540
gacgtgggcg tggataacgc tggcgcgaaa gcgggtctga ccttcctggt tgacctgatt    600
aaaaacaaac acatgaatgc agacaccgat tactccatcg cagaagctgc ctttaataaa    660
ggcgaaacag cgatgaccat caacggcccg tgggcatggt ccaacatcga caccagcaaa    720
gtgaattatg gtgtaacggt actgccgacc ttcaagggtc aaccatccaa accgttcgtt    780
ggcgtgctga gcgcaggtat taacgccgcc agtccgaaca aagagctggc aaaagagttc    840
ctcgaaaact atctgctgac tgatgaaggt ctggaagcgg ttaataaaga caaaccgctg    900
ggtgccgtag cgctgaagtc ttacgaggaa gagttggcga agatccacg tattgccgcc    960 actatggaaa acgcccagaa aggtgaaatc atgccgaaca tcccgcagat gtccgctttc   1020
tggtatgccg tgcgtactgc ggtgatcaac gccgccagcg tcgtcagac tgtcgatgaa   1080 gccctgaaag acgcgcagac taattcgagc tcgaacaaca acaacaataa caataacaac   1140
aacctcggga tcgagggaag gatttcagaa ttcggatcct ctagaatgct cggctacgtt   1200
ctcgcccgga tcggccagtc ggccatcgtg ctgctggcgg tcttcagcct ggtgttctgg   1260
ggcgtcagca tcctgccggc cgatccggcg gcgatcttcg tggccaaggg ggagggctac   1320
ttcaaccccg acatcgtcgc gcaggtcaag gcgttctacg gctacgaccg gccgctgtgg   1380
gtgcagtact tcgcgcagct gaaccaggtg ctgcacgggc atttcggctt ctcgctgtcc   1440
agcggtcagg ccgtcaccga ccggatcggc ggggtgatcg gcgagaccct gaaactggcg   1500
gccaccgcca ccgggttcgc ggtgctgttc gcggtgtcgg tcaccgcgct ggcgaccacc   1560
tgcgcgccgg tgcggtcggt gctgcgcgcg atcccgccgc tgttcggcgc ggtccccacg   1620
ttttga                                                              1626

<210> SEQ ID NO 10
<211> LENGTH: 1920
<212> TYPE: DNA
<213> ORGANISM: Mycobacterium avium

<400> SEQUENCE: 10
atgaaaatcg aagaaggtaa actggtaatc tggattaacg gcgataaagg ctataacggt     60
ctcgctgaag tcggtaagaa attcgagaaa gataccggaa ttaaagtcac cgttgagcat    120
ccggataaac tggaagagaa attcccacag gttgcggcaa ctggcgatgg ccctgacatt    180
atcttctggg cacacgaccg ctttggtggc tacgctcaat ctggcctgtt ggctgaaatc    240
accccggaca aagcgttcca ggacaagctg tatccgttta cctgggatgc cgtacgttac    300
aacggcaagc tgattgctta cccgatcgct gttgaagcgt tatcgctgat ttataacaaa    360
gatctgctgc cgaacccgcc aaaaacctgg gaagagatcc cggcgctgga taagaaactg    420
aaagcgaaag gtaagagcgc gctgatgttc aacctgcaag aaccgtactt cacctggccg    480
ctgattgctg ctgacggggg ttatgcgttc aagtatgaaa acggcaagta cgacattaaa    540
gacgtgggcg tggataacgc tggcgcgaaa gcgggtctga ccttcctggt tgacctgatt    600
aaaaacaaac acatgaatgc agacaccgat tactccatcg cagaagctgc ctttaataaa    660
ggcgaaacag cgatgaccat caacggcccg tgggcatggt ccaacatcga caccagcaaa    720
gtgaattatg gtgtaacggt actgccgacc ttcaagggtc aaccatccaa accgttcgtt    780
ggcgtgctga gcgcaggtat taacgccgcc agtccgaaca aagagctggc aaaagagttc    840
ctcgaaaact atctgctgac tgatgaaggt ctggaagcgg ttaataaaga caaaccgctg    900
```

-continued ggtgccgtag cgctgaagtc ttacgaggaa gagttggcga aagatccacg tattgccgcc 960
actatggaaa acgcccagaa aggtgaaatc atgccgaaca tcccgcagat gtccgctttc 1020
tggtatgccg tgcgtactgc ggtgatcaac gccgccagcg gtcgtcagac tgtcgatgaa 1080
gccctgaaag acgcgcagac taattcgagc tcgaacaaca acaacaataa caataacaac 1140
aacctcggga tcgagggaag gatttcagaa ttcggatcct ctagaatgcg ccgcaaccgg 1200
tttcgtctca tcgtcttcgc ctggatcacc gcgatggtga ccgggctgat gttttccgtg 1260
gcaccgacgc cggccgcgct ggccgacccc ggcgagtggg atcccaccct gccggcccag 1320
atcagtgccg gcgccccggg cgatccgctc gccgtcgcca acgcctcgct gcaggccacc 1380
gcgcaggcca cccagaccac gctgaacctg ggcaagcaat tcctcggcgg gctcggcatc 1440
aacctgggcg gcaacgacgc gcccgcggcc gcggccacgc cgtccaaccc gggcggcaag 1500
atcccgcggg tctacggccg gcaggccatc gagtacgtga tcaagcggat ggggtcgcag 1560
atgggggtgc cgtactcgtg ggcggcggc tcgctggacg gtcccagcaa gggtgtcggc 1620
gacggcgcca acatcaccgg gttcgactgc tcggggctga tgcgctacgg cttcgccggg 1680
gtcggcgtgc tgatcccgcg gttctccggc gaccagtaca acgccgggcg tcacatcccg 1740
caggatcagg cccgccgcgg cgacctcatc ttctacggcc cgggcgggtc ccagcacgtc 1800
accatgtacc tgggcaacgg gcagatgctc gaggcgtccg gcagcgccgg caaggtcacc 1860
gtcagcccgg tgcgcaagcc cggcatgaca ccgttcctga ctaggatcat cgagtactga 1920

<210> SEQ ID NO 11
<211> LENGTH: 2136
<212> TYPE: DNA
<213> ORGANISM: Mycobacterium avium

<400> SEQUENCE: 11
atgaaaatcg aagaaggtaa actggtaatc tggattaacg gcgataaagg ctataacggt 60
ctcgctgaag tcggtaagaa attcgagaaa gataccggaa ttaaagtcac cgttgagcat 120
ccggataaac tggaagagaa attcccacag gttgcggcaa ctggcgatgg ccctgacatt 180
atcttctggg cacacgaccg ctttggtggc tacgctcaat ctggcctgtt ggctgaaatc 240
accccggaca aagcgttcca ggacaagctg tatccgttta cctgggatgc cgtacgttac 300
aacggcaagc tgattgctta cccgatcgct gttgaagcgt tatcgctgat ttataacaaa 360
gatctgctgc cgaacccgcc aaaaacctgg gaagagatcc cggcgctgga taaagaactg 420
aaagcgaaag gtaagagcgc gctgatgttc aacctgcaag aaccgtactt cacctggccg 480
ctgattgctg ctgacggggg ttatgcgttc aagtatgaaa acggcaagta cgacattaaa 540
gacgtgggcg tggataacgc tggcgcgaaa gcgggtctga ccttcctggt tgacctgatt 600
aaaaacaaac acatgaatgc agacaccgat tactccatcg cagaagctgc ctttaataaa 660
ggcgaaacag cgatgaccat caacggcccg tgggcatggt ccaacatcga caccagcaaa 720
gtgaattatg gtgtaacggt actgccgacc ttcaagggtc aaccatccaa accgttcgtt 780
ggcgtgctga gcgcaggtat taacgccgcc agtccgaaca aagagctggc aaaagagttc 840
ctcgaaaact atctgctgac tgatgaaggt ctggaagcgg ttaataaaga caaaccgctg 900
ggtgccgtag cgctgaagtc ttacgaggaa gagttggcga aagatccacg tattgccgcc 960
actatggaaa acgcccagaa aggtgaaatc atgccgaaca tcccgcagat gtccgctttc 1020
tggtatgccg tgcgtactgc ggtgatcaac gccgccagcg gtcgtcagac tgtcgatgaa 1080
gccctgaaag acgcgcagac taattcgagc tcgaacaaca acaacaataa caataacaac 1140

-continued

```
aacctcggga tcgagggaag gatttcagaa ttcggatcct ctagagtgcg atcccagcgt    1200
gggggtcctc gcccggtcca tgaaccgggg cggacgcgcg aggtcaccgc gccgaggccc    1260
gacgagtgcc ggagaggcca ggaaaggcca ggaaaaatga acgcatcta cgccttcgcg    1320 atcggtttgg ccctactcgg ggcgccgcg gcgccgatgt tggttccccc cgtcgcgacc    1380
gccgacccgg gcgtcagggc gatggactat cagcaggcca ccgacgtggt gatcgcgcgc    1440
ggtctgtcgc agcgcggtgt gccgttctcc tgggccggcg gcggcatcaa cggcccacc    1500 cgcggcaccg gaccggcgc caacaccgtc ggtttcgacg cgtccgggct gatgcagtac    1560
gcgtacgccg gcgccggcat caagctgccg cgctcgtccg gcgcgatgta ccgcgtcggc    1620
cagaagatcc tgccgcagca ggcccgcaag ggtgacctga tcttctacgg ccccgagggc    1680
acccagagcg tcgcaatgta cctgggcaac aaccagatgc tcgaggtcgg cgacgtggtg    1740
caggtgtcgc cggtgcgtac cgccggcatg gcgccctaca tggtccgggt gttgggaacc    1800
acggcgccca cccagcaggt tccgcagcag gcgccgctgc agcagacccc ggcgcagcag    1860
gcgcccttgc aacagacccc gggccagcag gcgcccttgc agcagacccc gggccagcaa    1920
ctgcccaccc agcaggcccc gctgcaacag gttccggggc agcaggttcc ggggcagcag    1980
ctgcccaccc agcaagcgcc ccagcaggca cccctgcagc tggcgccgac ccagcaggcg    2040
ccgctgcaac agctgccgac ccagcagtca ccgctgcagc agctgccggt ccagcagtcg    2100
ccactgcagc cggcgggcgc cggactcacc cggtag                              2136
```

<210> SEQ ID NO 12
<211> LENGTH: 1515
<212> TYPE: DNA
<213> ORGANISM: Mycobacterium avium

<400> SEQUENCE: 12

```
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgtttta cctgggatgc cgtacgttac     300
aacggcaagc tgattgctta cccgatcgct gttgaagcgt atcgctgat ttataacaaa     360 gatctgctgc cgaacccgcc aaaaacctgg gaagagatcc cggcgctgga taagaactg     420 aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtggcgc tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga cgcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc     960 actatggaaa acgcccagaa aggtgaaatc atgccgaaca tcccgcagat gtccgctttc    1020
tggtatgccg tgcgtactgc ggtgatcaac gccgccagcg tcgtcagac tgtcgatgaa    1080
```

```
gccctgaaag acgcgcagac taattcgagc tcgaacaaca acaacaataa caataacaac    1140
aacctcggga tcgagggaag gatttcagaa ttcggatcct ctagaatggt caccccgctg    1200
acgctggaca ccggccgtgg tagcgacggc aacccggtgc tggtggcagt gggcgaaatc    1260
gacctgagca acatcgacgc attccaccgg gcgctggcca ccgccaccgc ggaggtcacc    1320
gggagtgacg gcgcggtgct cgtcgacctc agcgccgtgg agtatgtgga cagcgccgcc    1380
atcaatgcgt tggccgcgca cgccgaccac atcgcgctcg tcgcgcaccc ggtcctgatg    1440
cccgtcttca gggtcagcgg tttgaccgag ctgaccaccg tcgaagccgc accccgccg     1500 ccggcgcctc gttga                                                    1515
```